US006555658B2

(12) United States Patent
Trinchieri et al.

(10) Patent No.: US 6,555,658 B2
(45) Date of Patent: *Apr. 29, 2003

(54) ANTIBODIES TO NATURAL KILLER STIMULATORY FACTOR

(75) Inventors: Giorgio Trinchieri, Wynnewood, PA (US); Bice Perussia, Philadelphia, PA (US); Steven C. Clark, Winchester, MA (US); Gordon G. Wong, Jamaica Plain, MA (US); Rodney Hewick, Lexington, MA (US); Michiko Kobayashi, Brookline, MA (US)

(73) Assignees: Wyeth, Madison, NJ (US); The Wistar Institute, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,703

(22) Filed: Aug. 9, 2001

(65) Prior Publication Data

US 2002/0137898 A1 Sep. 26, 2002

Related U.S. Application Data

(60) Division of application No. 09/325,958, filed on Jun. 4, 1999, now Pat. No. 6,300,478, which is a division of application No. 08/858,000, filed on May 16, 1997, now abandoned, which is a continuation of application No. 08/403,013, filed on Mar. 13, 1995, now Pat. No. 5,648,467, which is a division of application No. 07/584,941, filed on Sep. 18, 1990, now Pat. No. 5,457,038, which is a continuation-in-part of application No. 07/307,817, filed on Feb. 7, 1989, now abandoned, which is a continuation-in-part of application No. 07/269,945, filed on Nov. 10, 1988, now abandoned.

(51) Int. Cl.[7] .............................................. C07K 16/24
(52) U.S. Cl. ................................ 530/388.1; 530/388.23
(58) Field of Search ........................... 530/387.9, 388.1, 530/388.23, 388.24, 351

(56) References Cited

U.S. PATENT DOCUMENTS

| 4,473,555 A | | 9/1984 | Nestor, Jr. et al. ........... 424/177 |
| 5,811,523 A | * | 9/1998 | Trinchieri et al. ....... 530/387.9 |

FOREIGN PATENT DOCUMENTS

| EP | 0357 067 B1 | 3/1990 |
| EP | 0433 827 A2 | 6/1991 |

OTHER PUBLICATIONS

Kobayashi, et al., "Identification and Purification of Natural Killer Cell Stimulatory Factor (NKSF), A Cytokine with Multiple Biologic Effects on Human Lymphocytes," *The Journal of Experimental Medicine*, 170(4): 827–845 (1989).
Lanier, et al., "Interleukin 2 Activation of Natural Killer Cells Rapidly Induces the Expression and Phosphorylation of the Leu–23 Activation Antigen," *The Journal of Experimental Medicine*, 167(5): 1572–1585 (1988).

Ling, et al., "Human IL–12 p40 Homodimer Binds to the IL–12 Receptor but Does Not Mediate Biologic Activity," *The Journal of Immunology*, 154(1): 116–127 (1995).
Mattner, et al., "The Interleukin–12 Subunit p40 Specifically Inhibits Effects of the Interleukin–12 Heterodimer," *European Journal of Immunology*, 23(9): 2202–2208 (1993).
Petrányi, et al., "Natural Killer Cells in Man: Genetic and Other Factors Regulating Their Activity," *Progress in Immunology V*, 1169–1180 (1983).
Richard, et al., "Cytokines Involved in the Augmentation of Murine Natural Killer Cell Activity by Pyrimidinones in Vivo," *Journal of Biological Response Modifiers*, 6(6): 647–663 (1987).
Sinosich, et al., "Affinity Immunoelectrophoresis and Chromatography for Isolation and Characterization of a Placental Granulocyte Elastase Inhibitor," *Protein Purification: Micro to Macro, Proceedings of a Cetus–UCLA Sumposium*, pp. 225–238 (1987).
Stern, et al., "Purification to Homogeneity and Partial Characterization of Cytoxic Lymphocyte Maturation Factor From Human B–Lymphoblastoid Cells," *Proceedings of the National Academy of Sciences*, 87(17): 6808–6812 (1990).
Talmadge, "Immunoregulation and Immunostimulation of Murine Lymphocytes by Recombinant Human Interleukin–2," *Journal of Biological Response Modifiers*, 4(1): 18–34 (1985).
Wasserman, et al., "Purification and Characterization of Recombinant Human Malaria Vaccine Candidates from *E. Coli*," *Protein Purification: Micro to Macro*, 337–354 (1987).
Wei, et al., "Covalent Structure of Three Phase–1 Flagellar Filament Proteins of Salmonella," *Journal of Molecular Biology*, 186(4): 791–803 (1985).
Wong, et al., "Multiple Actions of Interleukin 6 Within a Cytokine Network," *Immunology Today*, 9(5): 137–139 (1988).
Wong, et al., "Characterization of a Factor(s) Which Synergizes with Recombinant Interleukin 2 in Promoting Allogeneic Human Cytolytic T–Lymphocyte Responses In Vitro," *Cellular Immunology*, 111(1): 39–54 (1988).
Cohen, "IL–12 Deaths Explanations and a Puzzle," *Science* 270: 908 (1995).
Casagli, et al., "Purification of Recombinant Human Interleukin 1β Produced From Yeast," *Protein Purification: Micro to Macro, Proceedings of a Cetus–UCLA Sumposium*, pp. 421–427 (1987).

(List continued on next page.)

Primary Examiner—Prema Mertz
(74) Attorney, Agent, or Firm—Finnegan, Henderson, Farabow, Garrett & Dunner, L.L.P.

(57) ABSTRACT

This application relates to antibodies reactive with a novel homogenous human cytokine, Natural Killer Stimulator Factor (NKSF), having the ability to induce the production of gamma interferon in vitro in human peripheral blood lymphocytes, and a pharmaceutical preparation containing such antibodies.

4 Claims, 7 Drawing Sheets

OTHER PUBLICATIONS

Devos, et al., "Molecular Cloning of Human Interleukin 2 cDNA and its Expression in *E. coli,*" *Nucleic Acids Research*, 11(13): 4307–4323 (1983).

Herberman, et al., "Natural Killer Cells: Their Role in Defenses Against Disease," *Science*, 214: 24–30 (1981).

Ichimura, et al., "Characterization of Mouse Natural Killer Cell Activating Factor (NKAF) induced by OK–432: Evidence for Interferon–and Interleukin 2–Independent NK Cell Activation," *The British Journal of Cancer*, 50(1): 97–108 (1984).

Katayama, et al., "Comparison of Amino Acid Sequence of Bovine Coagulation Factor IX (Christmas Factor) with that of Other Vitamin K–Dependent Plasma Proteins," *Proceedings of the National Academy of Sciences*, 76(10): 4990–4994 (1979).

\* cited by examiner

FIG 1A

```
GAATTCCGTC GACTCTAGAG GCCCAGAGCA AG ATG TGT CAC CAG          44
                                   Met Cys His Gln
                                    1

CAG TTG GTC ATC TCT TGG TTT TCC CTG GTT TTT CTG GCA          83
Gln Leu Val Ile Ser Trp Phe Ser Leu Val Phe Leu Ala
 5               10                  15

TCT CCC CTC GTG GCC ATA TGG GAA CTG AAG AAA GAT GTT         122
Ser Pro Leu Val Ala Ile Trp Glu Leu Lys Lys Asp Val
         20              25                  30

TAT GTC GTA GAA TTG GAT TGG TAT CCG GAT GCC CCT GGA         161
Tyr Val Val Glu Leu Asp Trp Tyr Pro Asp Ala Pro Gly
                 35                  40

GAA ATG GTG GTC CTC ACC TGT GAC ACC CCT GAA GAA GAT         200
Glu Met Val Val Leu Thr Cys Asp Thr Pro Glu Glu Asp
 45                      50                  55

GGT ATC ACC TGG ACC TTG GAC CAG AGC AGT GAG GTC TTA         239
Gly Ile Thr Trp Thr Leu Asp Gln Ser Ser Glu Val Leu
             60                  65

GGC TCT GGC AAA ACC CTG ACC ATC CAA GTC AAA GAG TTT         278
Gly Ser Gly Lys Thr Leu Thr Ile Gln Val Lys Glu Phe
 70              75                  80

GGA GAT GCT GGC CAG TAC ACC TGT CAC AAA GGA GGC GAG         317
Gly Asp Ala Gly Gln Tyr Thr Cys His Lys Gly Gly Glu
             85                  90                  95

GTT CTA AGC CAT TCG CTC CTG CTT CAC AAA AAG GAA            356
Val Leu Ser His Ser Leu Leu Leu His Lys Lys Glu
                 100                 105

GAT GGA ATT TGG TCC ACT GAT ATT TTA AAG GAC CAG AAA         395
Asp Gly Ile Trp Ser Thr Asp Ile Leu Lys Asp Gln Lys
 110                 115                 120
```

FIG 1B

| | | | | | | | | | | | | |
|---|---|---|---|---|---|---|---|---|---|---|---|---|
| GAA | CCC | AAA | AAT | AAG | ACC | TTT | CTA | AGA | TGC | GAG | GCC | AAG | 434 |
| Glu | Pro | Lys | Asn | Lys | Thr | Phe | Leu | Arg | Cys | Glu | Ala | Lys | |
| | | | 125 | | | | | 130 | | | | | |

| AAT | TAT | TCT | GGA | CGT | TTC | ACC | TGC | TGG | TGG | CTG | ACG | ACA | 473 |
|---|---|---|---|---|---|---|---|---|---|---|---|---|---|
| Asn | Tyr | Ser | Gly | Arg | Phe | Thr | Cys | Trp | Trp | Leu | Thr | Thr | |
| 135 | | | | | 140 | | | | | 145 | | | |

| ATC | AGT | ACT | GAT | TTG | ACA | TTC | AGT | GTC | AAA | AGC | AGC | AGA | 512 |
|---|---|---|---|---|---|---|---|---|---|---|---|---|---|
| Ile | Ser | Thr | Asp | Leu | Thr | Phe | Ser | Val | Lys | Ser | Ser | Arg | |
| | | 150 | | | | | 155 | | | | | 160 | |

| GGC | TCT | TCT | GAC | CCC | CAA | GGG | GTG | ACG | TGC | GGA | GCT | GCT | 551 |
|---|---|---|---|---|---|---|---|---|---|---|---|---|---|
| Gly | Ser | Ser | Asp | Pro | Gln | Gly | Val | Thr | Cys | Gly | Ala | Ala | |
| | | | | 165 | | | | | 170 | | | | |

| ACA | CTC | TCT | GCA | GAG | AGA | GTC | AGA | GGG | GAC | AAC | AAG | GAG | 590 |
|---|---|---|---|---|---|---|---|---|---|---|---|---|---|
| Thr | Leu | Ser | Ala | Glu | Arg | Val | Arg | Gly | Asp | Asn | Lys | Glu | |
| | 175 | | | | | 180 | | | | | 185 | | |

| TAT | GAG | TAC | TCA | GTG | GAG | TGC | CAG | GAG | GAC | AGT | GCC | TGC | 629 |
|---|---|---|---|---|---|---|---|---|---|---|---|---|---|
| Tyr | Glu | Tyr | Ser | Val | Glu | Cys | Gln | Glu | Asp | Ser | Ala | Cys | |
| | | | 190 | | | | | 195 | | | | | |

| CCA | GCT | GCT | GAG | GAG | AGT | CTG | CCC | ATT | GAG | GTC | ATG | GTG | 668 |
|---|---|---|---|---|---|---|---|---|---|---|---|---|---|
| Pro | Ala | Ala | Glu | Glu | Ser | Leu | Pro | Ile | Glu | Val | Met | Val | |
| 200 | | | | | 205 | | | | | 210 | | | |

| GAT | GCC | GTT | CAC | AAG | CTC | AAG | TAT | GAA | AAC | TAC | ACC | AGC | 707 |
|---|---|---|---|---|---|---|---|---|---|---|---|---|---|
| Asp | Ala | Val | His | Lys | Leu | Lys | Tyr | Glu | Asn | Tyr | Thr | Ser | |
| | | | 215 | | | | 220 | | | | | 225 | |

| AGC | TTC | TTC | ATC | AGG | GAC | ATC | ATC | AAA | CCT | GAC | CCA | CCC | 746 |
|---|---|---|---|---|---|---|---|---|---|---|---|---|---|
| Ser | Phe | Phe | Ile | Arg | Asp | Ile | Ile | Lys | Pro | Asp | Pro | Pro | |
| | | | | 230 | | | | 235 | | | | | |

| AAG | AAC | TTG | CAG | CTG | AAG | CCA | TTA | AAG | AAT | TCT | CGG | CAG | 785 |
|---|---|---|---|---|---|---|---|---|---|---|---|---|---|
| Lys | Asn | Leu | Gln | Leu | Lys | Pro | Leu | Lys | Asn | Ser | Arg | Gln | |
| | | 240 | | | | | 245 | | | | | 250 | |

| GTG | GAG | GTC | AGC | TGG | GAG | TAC | CCT | GAC | ACC | TGG | AGT | ACT | 824 |
|---|---|---|---|---|---|---|---|---|---|---|---|---|---|
| Val | Glu | Val | Ser | Trp | Glu | Tyr | Pro | Asp | Thr | Trp | Ser | Thr | |
| | | | | 255 | | | | | 260 | | | | |

| CCA | CAT | TCC | TAC | TTC | TCC | CTG | ACA | TTC | TGC | GTT | CAG | GTC | 863 |
|---|---|---|---|---|---|---|---|---|---|---|---|---|---|
| Pro | His | Ser | Tyr | Phe | Ser | Leu | Thr | Phe | Cys | Val | Gln | Val | |
| 265 | | | | | 270 | | | | | 275 | | | |

| CAG | GGC | AAG | AGC | AAG | AGA | GAA | AAG | AAA | GAT | AGA | GTC | TTC | 902 |
|---|---|---|---|---|---|---|---|---|---|---|---|---|---|
| Gln | Gly | Lys | Ser | Lys | Arg | Glu | Lys | Lys | Asp | Arg | Val | Phe | |
| | | | 280 | | | | | 285 | | | | 290 | |

FIG 1C

```
ACG GAC AAG ACC TCA GCC ACG GTC ATC TGC CGC AAA AAT        941
Thr Asp Lys Thr Ser Ala Thr Val Ile Cys Arg Lys Asn
            295             300

GCC AGC ATT AGC GTG CGG GCC CAG GAC CGC TAC TAT AGC        980
Ala Ser Ile Ser Val Arg Ala Gln Asp Arg Tyr Tyr Ser
        305             310             315

TCA TCT TGG AGC GAA TGG GCA TCT GTG CCC TGC AGT TAG       1019
Ser Ser Trp Ser Glu Trp Ala Ser Val Pro Cys Ser  *
            320             325
```

| Sequence | Position |
|---|---|
| GTTCTGATCC AGGATGAAAA TTTGGAGGAA AAGTGGAAGA | 1059 |
| TATTAAGCAA AATGTTTAAA GACACAACGG AATAGACCCA | 1099 |
| AAAAGATAAT TTCTATCTGA TTTGCTTTAA AACGTTTTTT | 1139 |
| TAGGATCACA ATGATATCTT TGCTGTATTT GTATAGTTCG | 1179 |
| ATGCTAAATG CTCATTGAAA CAATCAGCTA ATTTATGTAT | 1219 |
| AGATTTTCCA GCTCTCAAGT TGCCATGGGC CTTCATGCTA | 1259 |
| TTTAAATATT TAAGTAATTT ATGTATTTAT TAGTATATTA | 1299 |
| CTGTTATTTA ACGTTTGTCT GCCAGGATGT ATGGAATGTT | 1339 |
| TCATACTCTT ATGACCTGAT CCATCAGGAT CAGTCCCTAT | 1379 |
| TATGCAAAAT GTGAATTTAA TTTTATTTGT ACTGACAACT | 1419 |
| TTTCAAGCAA GGCTGCAAGT ACATCAGTTT TATGACAATC | 1459 |
| AGGAAGAATG CAGTGTTCTG ATACCAGTGC CATCATACAC | 1499 |
| TTGTGATGGA TGGGAACGCA AGAGATACTT ACATGGAAAC | 1539 |
| CTGACAATGC AAACCTGTTG AGAAGATCCA GGAGAACAAG | 1579 |
| ATGCTAGTTC CCATGTCTGT GAAGACTTCC TGGAGATGGT | 1619 |
| GTTGATAAAG CAATTTAGGG CCACTTACAC TTCTAAGCAA | 1659 |
| GTTTAATCTT TGGATGCCTG AATTTTAAAA GGGCTAGAAA | 1699 |
| AAAATGATTG ACCAGCCTGG GAAACATAAC AAGACCCCGT | 1739 |
| CTCTACAAAA AAAATTTAAA ATTAGCCAGG CGTGGTGGCT | 1779 |

FIG 1D

| | |
|---|---|
| CATGCTTGTG GTCCCAGCTG TTCAGGAGGA TGAGGCAGGA | 1819 |
| GGATCTCTTG AGCCCAGGAG GTCAAGGCTA TGGTGAGCCG | 1859 |
| TGATTGTGCC ACTGCATACC AGCCTAGGTG ACAGAATGAG | 1899 |
| ACCCTGTCTC AAAAAAAAA ATGATTGAAA TTAAAATTCA | 1939 |
| GCTTTAGCTT CCATGGCAGT CCTCACCCCC ACCTCTCTAA | 1979 |
| AAGACACAGG AGGATGACAC AGAAACACCG TAAGTGTCTG | 2019 |
| GAAGGCAAAA AGATCTTAAG ATTCAAGAGA GAGGACAAGT | 2059 |
| AGTTATGGCT AAGGACATGA AATTGTCAGA ATGGCAGGTG | 2099 |
| GCTTCTTAAC AGCCATGTGA GAAGCAGACA GATGCAAAGA | 2139 |
| AAATCTGGAA TCCCTTTCTC ATTAGCATGA ATGAACCTGA | 2179 |
| TACACAATTA TGACCAGAAA ATATGGCTCC ATGAAGGTGC | 2219 |
| TACTTTTAAG TAATGTATGT GCGCTCTGTA AAGTGATTAC | 2259 |
| ATTTGTTTCC TGTTTGTTTA TTTATTTATT TATTTTTGCA | 2299 |
| TTCTGAGGCT GAACTAATAA AAACTCTTCT TTGTAATCAA | 2339 |
| AAAAAAAAA AAAAAACTCT AGA | 2362 |

FIG 2A

```
GTCGACTCTA GAG GTCACCGAGA AGCTGATGTA GAGAGAGACA         30
polylinker  *
            nucleotide #1 of p35nksf14-1-1

CAGAAGGAGA CAGAAAGCAA GAGACCAGAG TCCCGGGAAA             70

GTCCTGCCGC GCCTCGGGAC AATTATAAAA                        100

ATG TGG CCC CCT GGG TCA GCC TCC                         124
Met Trp Pro Pro Gly Ser Ala Ser
 1               5

* (nucleotide #1 of p35nksf9-1-1)
CAG CCA CCG CCC TCA CCT GCC GCG GCC ACA GGT CTG CAT     163
Gln Pro Pro Pro Ser Pro Ala Ala Ala Thr Gly Leu His
     10              15                  20

Pst I
CCA GCG GCT CGC CCT GTG TCC CTG CAG TGC CGG CTC AGC     202
Pro Ala Ala Arg Pro Val Ser Leu Gln Cys Arg Leu Ser
         25              30

ATG TGT CCA GCG CGC AGC CTC CTC CTT GTG GCT ACC CTG     241
Met Cys Pro Ala Arg Ser Leu Leu Leu Val Ala Thr Leu
 35              40                  45

GTC CTC CTG GAC CAC CTC AGT TTG GCC AGA AAC CTC CCC     280
Val Leu Leu Asp His Leu Ser Leu Ala Arg Asn Leu Pro
         50              55                  60

GTG GCC ACT CCA GAC CCA GGA ATG TTC CCA TGC CTT CAC     319
Val Ala Thr Pro Asp Pro Gly Met Phe Pro Cys Leu His
             65                  70

CAC TCC CAA AAC CTG CTG AGG GCC GTC AGC AAC ATG CTC     358
His Ser Gln Asn Leu Leu Arg Ala Val Ser Asn Met Leu
 75              80                  85
```

FIG 2B

```
CAG AAG GCC AGA CAA ACT CTA GAA TTT TAC CCT TGC ACT    397
Gln Lys Ala Arg Gln Thr Leu Glu Phe Tyr Pro Cys Thr
        90                      95

TCT GAA GAG ATT GAT CAT GAA GAT ATC ACA AAA GAT AAA    436
Ser Glu Glu Ile Asp His Glu Asp Ile Thr Lys Asp Lys
100             105                     110

ACC AGC ACA GTG GAG GCC TGT TTA CCA TTG GAA TTA ACC    475
Thr Ser Thr Val Glu Ala Cys Leu Pro Leu Glu Leu Thr
        115                     120                 125

AAG AAT GAG AGT TGC CTA AAT TCC AGA GAG ACC TCT TTC    514
Lys Asn Glu Ser Cys Leu Asn Ser Arg Glu Thr Ser Phe
                130                     135

ATA ACT AAT GGG AGT TGC CTG GCC TCC AGA AAG ACC TCT    553
Ile Thr Asn Glu Ser Cys Leu Ala Ser Arg Lys Thr Ser
        140                     145                 150

TTT ATG ATG GCC CTG TGC CTT AGT AGT ATT TAT GAA GAC    592
Phe Met Met Ala Leu Cys Leu Ser Ser Ile Tyr Glu Asp
                155                     160

TTG AAG ATG TAC CAG GTG GAG TTC AAG ACC ATG AAT GCA    631
Leu Lys Met Tyr Gln Val Glu Phe Lys Thr Met Asn Ala
165             170                     175

AAG CTT CTG ATG GAT CCT AAG AGG CAG ATC TTT CTA GAT    670
Lys Leu Leu Met Asp Pro Lys Arg Gln Ile Phe Leu Asp
        180                     185                 190

CAA AAC ATG CTG GCA GTT ATT GAT GAG CTG ATG CAG GCC    709
Gln Asn Met Leu Ala Val Ile Asp Glu Leu Met Gln Ala
                195                     200

CTG AAT TTC AAC AGT GAG ACT GTG CCA CAA AAA TCC TCC    748
Leu Asn Phe Asn Ser Glu Thr Val Pro Gln Lys Ser Ser
        205                     210                 215

CTT GAA GAA CCG GAT TTT TAT AAA ACT AAA ATC AAG CTC    787
Leu Glu Glu Pro Asp Phe Tyr Lys Thr Lys Ile Lys Leu
                220                     225

TGC ATA CTT CTT CAT GCT TTC AGA ATT CGG GCA GTG ACT    826
Cys Ile Leu Leu His Ala Phe Arg Ile Arg Ala Val Tyr
230             235                     240

ATT GAT AGA GTG ATG AGC TAT CTG AAT GCT TCC            860
Ile Asp Arg Val Met Ser Tyr Leu Asn Ala Ser
        245                     250
```

FIG 2C

| | | | | |
|---|---|---|---|---|
| TAAAAAAGCG | AGGTCCCTCC | AAACCGTTGT | CATTTTTATA | 900 |
| AAACTTTGAA | ATGAGGAAAC | TTTGATAGGA | TGTGGATTAA | 940 |
| GAACTAGGGA | GGGGGAAAGA | AGGATGGGAC | TATTACATCC | 980 |
| ACATGATACC | TCTGATCAAG | TATTTTTGAC | ATTTACTGTG | 1020 |
| GATAAATTGT | TTTTAAGTTT | TCATGAATGA | ATTGCTAAGA | 1060 |
| AGGGAAAATA | TCCATCCTGA | AGGTGTTTTT | CATTCACTTT | 1100 |
| AATAGAAGGG | CAAATATTTA | TAAGCTATTT | CTGTACCAAA | 1140 |
| GTGTTTGTGG | AAACAAACAT | GTAAGCATAA | CTTATTTTAA | 1180 |
| AATATTTATT | TATATAACTT | GGTAATCATG | AAAGCATCTG | 1220 |
| AGCTAACTTA | TATTTATTTA | TGTTATATTT | ATTAAATTAT | 1260 |
| TCATCAAGTG | TATTTGAAAA | ATATTTTTAA | GTGTTCTAAA | 1300 |

(last nucleotide of small clone, p35nksf)
\*
AATAAAAGTA TTGAATTAAA AAAAAAAAAA AAAAAAAAA        1340

\* polylinker
AAAAAAAAAA AAAAAAAAAA AAAA <u>CCTG CAGCCCGGGG GATCC</u>    1364
            last nucleotide in clone sequence though he

SEQUENCE LISTING

```
<160> NUMBER OF SEQ ID NOS: 19

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Trp Glu Leu Lys Lys Asp Val Tyr Val Val Glu Leu Asp Trp Tyr
 1               5                  10                  15

Pro Asp Ala Pro Gly Glu Met
            20

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Asn Leu Pro Val Ala Thr Pro Asp Pro Gly Met Phe Pro
 1               5                  10

<210> SEQ ID NO 3
<211> LENGTH: 2362
<212> TYPE: DNA
<213> ORGANISM: Artificial Sequence
<220> FEATURE:
<223> OTHER INFORMATION: Description of Artificial Sequence: Synthetic
      DNA sequence of the 40 kD subunit of NKSF
<221> NAME/KEY: CDS
<222> LOCATION: (33)..(1016)

<400> SEQUENCE: 3
```

-continued

```
gaattccgtc gactctagag gcccagagca ag atg tgt cac cag cag ttg gtc        53
                                    Met Cys His Gln Gln Leu Val
                                     1               5 atc tct tgg ttt tcc ctg gtt ttt ctg gca tct ccc ctc gtg gcc ata       101
Ile Ser Trp Phe Ser Leu Val Phe Leu Ala Ser Pro Leu Val Ala Ile
         10                  15                  20 tgg gaa ctg aag aaa gat gtt tat gtc gta gaa ttg gat tgg tat ccg       149
Trp Glu Leu Lys Lys Asp Val Tyr Val Val Glu Leu Asp Trp Tyr Pro
 25                  30                  35 gat gcc cct gga gaa atg gtg gtc ctc acc tgt gac acc cct gaa gaa       197
Asp Ala Pro Gly Glu Met Val Val Leu Thr Cys Asp Thr Pro Glu Glu
 40                  45                  50                  55 gat ggt atc acc tgg acc ttg gac cag agc agt gag gtc tta ggc tct       245
Asp Gly Ile Thr Trp Thr Leu Asp Gln Ser Ser Glu Val Leu Gly Ser
             60                  65                  70 ggc aaa acc ctg acc atc caa gtc aaa gag ttt gga gat gct ggc cag       293
Gly Lys Thr Leu Thr Ile Gln Val Lys Glu Phe Gly Asp Ala Gly Gln
         75                  80                  85 tac acc tgt cac aaa gga ggc gag gtt cta agc cat tcg ctc ctg ctg       341
Tyr Thr Cys His Lys Gly Gly Glu Val Leu Ser His Ser Leu Leu Leu
     90                  95                 100 ctt cac aaa aag gaa gat gga att tgg tcc act gat att tta aag gac       389
Leu His Lys Lys Glu Asp Gly Ile Trp Ser Thr Asp Ile Leu Lys Asp
105                 110                 115 cag aaa gaa ccc aaa aat aag acc ttt cta aga tgc gag gcc aag aat       437
Gln Lys Glu Pro Lys Asn Lys Thr Phe Leu Arg Cys Glu Ala Lys Asn
120                 125                 130                 135 tat tct gga cgt ttc acc tgc tgg tgg ctg acg aca atc agt act gat       485
Tyr Ser Gly Arg Phe Thr Cys Trp Trp Leu Thr Thr Ile Ser Thr Asp
            140                 145                 150 ttg aca ttc agt gtc aaa agc agc aga ggc tct tct gac ccc caa ggg       533
Leu Thr Phe Ser Val Lys Ser Ser Arg Gly Ser Ser Asp Pro Gln Gly
        155                 160                 165 gtg acg tgc gga gct gct aca ctc tct gca gag aga gtc aga ggg gac       581
Val Thr Cys Gly Ala Ala Thr Leu Ser Ala Glu Arg Val Arg Gly Asp
    170                 175                 180 aac aag gag tat gag tac tca gtg gag tgc cag gag gac agt gcc tgc       629
Asn Lys Glu Tyr Glu Tyr Ser Val Glu Cys Gln Glu Asp Ser Ala Cys
185                 190                 195 cca gct gct gag gag agt ctg ccc att gag gtc atg gtg gat gcc gtt       677
Pro Ala Ala Glu Glu Ser Leu Pro Ile Glu Val Met Val Asp Ala Val
200                 205                 210                 215 cac aag ctc aag tat gaa aac tac acc agc agc ttc ttc atc agg gac       725
His Lys Leu Lys Tyr Glu Asn Tyr Thr Ser Ser Phe Phe Ile Arg Asp
            220                 225                 230 atc atc aaa cct gac cca ccc aag aac ttg cag ctg aag cca tta aag       773
Ile Ile Lys Pro Asp Pro Pro Lys Asn Leu Gln Leu Lys Pro Leu Lys
        235                 240                 245 aat tct cgg cag gtg gag gtc agc tgg gag tac cct gac acc tgg agt       821
Asn Ser Arg Gln Val Glu Val Ser Trp Glu Tyr Pro Asp Thr Trp Ser
    250                 255                 260 act cca cat tcc tac ttc tcc ctg aca ttc tgc gtt cag gtc cag ggc       869
Thr Pro His Ser Tyr Phe Ser Leu Thr Phe Cys Val Gln Val Gln Gly
265                 270                 275 aag agc aag aga gaa aag aaa gat aga gtc ttc acg gac aag acc tca       917
Lys Ser Lys Arg Glu Lys Lys Asp Arg Val Phe Thr Asp Lys Thr Ser
280                 285                 290                 295 gcc acg gtc atc tgc cgc aaa aat gcc agc att agc gtg cgg gcc cag       965
Ala Thr Val Ile Cys Arg Lys Asn Ala Ser Ile Ser Val Arg Ala Gln
```

-continued

```
              300              305              310
gac cgc tac tat agc tca tct tgg agc gaa tgg gca tct gtg ccc tgc    1013
Asp Arg Tyr Tyr Ser Ser Ser Trp Ser Glu Trp Ala Ser Val Pro Cys
            315              320              325 agt taggttctga tccaggatga aatttggag gaaaagtgga agatattaag          1066
Ser caaaatgttt aaagacacaa cggaatagac ccaaaaagat aatttctatc tgatttgctt  1126
taaaacgttt ttttaggatc acaatgatat ctttgctgta tttctatagt tcgatgctaa  1186
atgctcattg aaacaatcag ctaatttatg tatagatttt ccagctctca agttgccatg  1246
ggccttcatg ctatttaaat atttaagtaa tttatgtatt tattagtata ttactgttat  1306
ttaacgtttg tctgccagga tgtatggaat gtttcatact cttatgacct gatccatcag  1366
gatcagtccc tattatgcaa aatgtgaatt taattttatt tgtactgaca acttttcaag  1426
caaggctgca agtacatcag ttttatgaca atcaggaaga atgcagtgtt ctgataccag  1486
tgccatcata cacttgtgat ggatgggaac gcaagagata cttacatgga aacctgacaa  1546
tgcaaacctg ttgagaagat ccaggagaac aagatgctag ttcccatgtc tgtgaagact  1606
tcctggagat ggtgttgata aagcaattta gggccactta cacttctaag caagtttaat  1666
ctttggatgc ctgaatttta aagggctag aaaaaaatga ttgaccagcc tgggaaacat   1726
aacaagaccc cgtctctaca aaaaaatttt aaaattagcc aggcgtggtg gctcatgctt  1786
gtggtcccag ctgttcagga ggatgaggca ggaggatctc ttgagcccag gaggtcaagg  1846
ctatggtgag ccgtgattgt gccactgcat accagcctag gtgacagaat gagaccctgt  1906
ctcaaaaaaa aaaatgattg aaattaaaat tcagctttag cttccatggc agtcctcacc  1966
cccacctctc taaaagacac aggaggatga cacagaaaca ccgtaagtgt ctggaaggca  2026
aaaagatctt aagattcaag agagaggaca agtagttatg ctaaggaca tgaaattgtc    2086 agaatggcag gtggcttctt aacagccatg tgagaagcag acagatgcaa agaaaatctg  2146
gaatcccttt ctcattagca tgaatgaacc tgatacacaa ttatgaccag aaaatatggc  2206
tccatgaagg tgctactttt aagtaatgta tgtgcgctct gtaaagtgat tacatttgtt  2266
tcctgtttgt ttatttattt atttattttt gcattctgag gctgaactaa taaaaactct  2326
tctttgtaat caaaaaaaaa aaaaaaaaac tctaga                           2362
```

<210> SEQ ID NO 4
<211> LENGTH: 328
<212> TYPE: PRT
<213> ORGANISM: Artificial Sequence
<220> FEATURE:
<223> OTHER INFORMATION: Description of Artificial Sequence: Synthetic
      amino acid sequence of the 40 kD subunit of NKSF

<400> SEQUENCE: 4

```
Met Cys His Gln Gln Leu Val Ile Ser Trp Phe Ser Leu Val Phe Leu
  1               5                  10                  15

Ala Ser Pro Leu Val Ala Ile Trp Glu Leu Lys Lys Asp Val Tyr Val
             20                  25                  30

Val Glu Leu Asp Trp Tyr Pro Asp Ala Pro Gly Glu Met Val Val Leu
         35                  40                  45

Thr Cys Asp Thr Pro Glu Glu Asp Gly Ile Thr Trp Thr Leu Asp Gln
     50                  55                  60

Ser Ser Glu Val Leu Gly Ser Gly Lys Thr Leu Thr Ile Gln Val Lys
 65                  70                  75                  80
```

```
Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 5
<211> LENGTH: 1395
<212> TYPE: DNA
<213> ORGANISM: Artificial Sequence
<220> FEATURE:
<223> OTHER INFORMATION: Description of Artificial Sequence: Synthetic
      DNA sequence of the 30 kD subunit of NKSF
<221> NAME/KEY: CDS
<222> LOCATION: (114)..(872)

<400> SEQUENCE: 5
gtcgactcta gaggtcaccg agaagctgat gtagagagag acacagaagg agacagaaag       60
caagagacca gagtcccggg aaagtcctgc cgcgcctcgg acaattata aaa atg          116
                                                           Met
                                                             1 tgg ccc cct ggg tca gcc tcc cag cca ccg ccc tca cct gcc gcg gcc       164
Trp Pro Pro Gly Ser Ala Ser Gln Pro Pro Pro Ser Pro Ala Ala Ala
            5                  10                  15 aca ggt ctg cat cca gcg gct cgc cct gtg tcc ctg cag tgc cgg ctc       212
Thr Gly Leu His Pro Ala Ala Arg Pro Val Ser Leu Gln Cys Arg Leu
        20                  25                  30 agc atg tgt cca gcg cgc agc ctc ctc ctt gtg gct acc ctg gtc ctc       260
Ser Met Cys Pro Ala Arg Ser Leu Leu Leu Val Ala Thr Leu Val Leu
    35                  40                  45
```

```
ctg gac cac ctc agt ttg gcc aga aac ctc ccc gtg gcc act cca gac    308
Leu Asp His Leu Ser Leu Ala Arg Asn Leu Pro Val Ala Thr Pro Asp
 50              55                  60                  65 cca gga atg ttc cca tgc ctt cac cac tcc caa aac ctg ctg agg gcc    356
Pro Gly Met Phe Pro Cys Leu His His Ser Gln Asn Leu Leu Arg Ala
                 70                  75                  80 gtc agc aac atg ctc cag aag gcc aga caa act cta gaa ttt tac cct    404
Val Ser Asn Met Leu Gln Lys Ala Arg Gln Thr Leu Glu Phe Tyr Pro
             85                  90                  95 tgc act tct gaa gag att gat cat gaa gat atc aca aaa gat aaa acc    452
Cys Thr Ser Glu Glu Ile Asp His Glu Asp Ile Thr Lys Asp Lys Thr
         100                 105                 110 agc aca gtg gag gcc tgt tta cca ttg gaa tta acc aag aat gag agt    500
Ser Thr Val Glu Ala Cys Leu Pro Leu Glu Leu Thr Lys Asn Glu Ser
     115                 120                 125 tgc cta aat tcc aga gag acc tct ttc ata act aat ggg agt tgc ctg    548
Cys Leu Asn Ser Arg Glu Thr Ser Phe Ile Thr Asn Gly Ser Cys Leu
130                 135                 140                 145 gcc tcc aga aag acc tct ttt atg atg gcc ctg tgc ctt agt agt att    596
Ala Ser Arg Lys Thr Ser Phe Met Met Ala Leu Cys Leu Ser Ser Ile
                150                 155                 160 tat gaa gac ttg aag atg tac cag gtg gag ttc aag acc atg aat gca    644
Tyr Glu Asp Leu Lys Met Tyr Gln Val Glu Phe Lys Thr Met Asn Ala
            165                 170                 175 aag ctt ctg atg gat cct aag agg cag atc ttt cta gat caa aac atg    692
Lys Leu Leu Met Asp Pro Lys Arg Gln Ile Phe Leu Asp Gln Asn Met
        180                 185                 190 ctg gca gtt att gat gag ctg atg cag gcc ctg aat ttc aac agt gag    740
Leu Ala Val Ile Asp Glu Leu Met Gln Ala Leu Asn Phe Asn Ser Glu
    195                 200                 205 act gtg cca caa aaa tcc tcc ctt gaa gaa ccg gat ttt tat aaa act    788
Thr Val Pro Gln Lys Ser Ser Leu Glu Glu Pro Asp Phe Tyr Lys Thr
210                 215                 220                 225 aaa atc aag ctc tgc ata ctt ctt cat gct ttc aga att cgg gca gtg    836
Lys Ile Lys Leu Cys Ile Leu Leu His Ala Phe Arg Ile Arg Ala Val
                230                 235                 240 act att gat aga gtg atg agc tat ctg aat gct tcc taaaaaagcg         882
Thr Ile Asp Arg Val Met Ser Tyr Leu Asn Ala Ser
            245                 250 aggtccctcc aaaccgttgt catttttata aaactttgaa atgaggaaac tttgatagga    942
tgtggattaa gaactaggga gggggaaaga aggatgggac tattacatcc acatgatacc   1002
tctgatcaag tattttttgac atttactgtg gataaattgt ttttaagttt tcatgaatga  1062
attgctaaga agggaaaata tccatcctga aggtgttttt cattcacttt aatagaaggg   1122
caaatattta taagctattt ctgtaccaaa gtgtttgtgg aaacaaacat gtaagcataa   1182
cttattttaa aatatttatt tatataactt ggtaatcatg aaagcatctg agctaactta   1242
tatttattta tgttatattt attaaattat tcatcaagtg tatttgaaaa atattttaa    1302 gtgttctaaa aataaaagta ttgaattaaa aaaaaaaaaa aaaaaaaaaa aaaaaaaaa    1362 aaaaaaaaaa aaaacctgca gcccggggga tcc                                1395

<210> SEQ ID NO 6
<211> LENGTH: 253
<212> TYPE: PRT
<213> ORGANISM: Artificial Sequence
<220> FEATURE:
<223> OTHER INFORMATION: Description of Artificial Sequence: Synthetic
      amino acid sequence of the 30 kD subunit of NKSF
```

<400> SEQUENCE: 6

```
Met Trp Pro Pro Gly Ser Ala Ser Gln Pro Pro Ser Pro Ala Ala
 1               5                  10                  15

Ala Thr Gly Leu His Pro Ala Ala Arg Pro Val Ser Leu Gln Cys Arg
             20                  25                  30

Leu Ser Met Cys Pro Ala Arg Ser Leu Leu Leu Val Ala Thr Leu Val
             35                  40                  45

Leu Leu Asp His Leu Ser Leu Ala Arg Asn Leu Pro Val Ala Thr Pro
         50                  55                  60

Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                 85                  90                  95

Pro Cys Thr Ser Glu Glu Ile Asp His Glu Asp Ile Thr Lys Asp Lys
                100                 105                 110

Thr Ser Thr Val Glu Ala Cys Leu Pro Leu Glu Leu Thr Lys Asn Glu
            115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Leu Thr Ile Gln Val
 1               5
```

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Lys Tyr Glu Asn Tyr Thr
 1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Trp Glu Leu Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Met Asp Pro Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Met Ser Tyr Leu Asn Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Val Ser Asn Met Leu Gln Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ala Ser Ile Ser Val
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Thr Phe Leu Arg
  1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ile Ile Lys Pro Asp Pro Pro Lys
  1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Ser Tyr Leu Asn Ala
  1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Met Ser Tyr Leu Asn
  1               5

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcaggcgag cctgaattcc tcga                                           24

<210> SEQ ID NO 19
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgaggttaaa aaacgtctag gccccccgaa ccacggggac gtggttttcc tttgaaaaac   60
acgattgc                                                            68
```

ANTIBODIES TO NATURAL KILLER STIMULATORY FACTOR This is a division of application Ser. No. 09/325,958, filed Jun. 4, 1999; now U.S. Pat. No. 6,300,478 which was a division of application Ser. No. 08/858,000, filed May 16, 1997, now abandoned; which was a continuation of application Ser. No. 08/403,013, filed Mar. 13, 1995 and issued as U.S. Pat. No. 5,648,467; which was a division of application Ser. No. 07/584,941 filed Sep. 18, 1990 and issued as U.S. Pat. No. 5,457,038, which was a continuation-in-part of Ser. No. 07/307,817, filed Feb. 7, 1989, now abandoned; which was a continuation-in-part of Ser. No. 07/269,945, filed Nov. 10, 1988, now abandoned, all of which are incorporated herein by reference.

The present invention relates to a novel cytokine that stimulates the function of natural killer cells and other cells of the immune system, and to processes for obtaining the factor in homogeneous form and producing it by recombinant genetic engineering techniques.

BACKGROUND OF THE INVENTION

Natural killer (NK) cells are a subset of lymphocytes active in the immune system and representing an average 15% of mononuclear cells in human peripheral blood [G. Trinchieri and B. Perussia, *Lab. Invest.*, 50:489 (1984)]. Among the surface markers used to identify human NK cells is a receptor binding with low affinity to the Fc fragment of IgG antibodies, such as Fc-gamma receptor III or CD16 antigen [B. Perussia et al, *J. Immunol.*, 133:180 (1984)]. NK cells have been demonstrated to play an important role in vivo in the defense against tumors, tumor metastases, virus infection, and to regulate normal and malignant hematopoiesis.

A growing family of regulatory proteins that deliver signals between cells of the immune system has been identified. These regulatory molecules are known as cytokines. Many of the cytokines have been found to control the growth, development and biological activities of cells of the hematopoietic and immune systems. These regulatory molecules include all of the colony-stimulating factors (GM-CSF, G-CSF, M-CSF, and multi CSF or interleukin-3), the interleukins (IL-1 through IL-11), the interferons (alpha, beta and gamma), the tumor necrosis factors (alpha and beta) and leukemia inhibitory factor (LIF). These cytokines exhibit a wide range of biologic activities with target cells from bone marrow, peripheral blood, fetal liver, and other lymphoid or hematopoietic organs. See, e.g., G. Wong and S. Clark, *Immunology Today*, 9(5):137 (1988).

The biochemical and biological identification and characterization of certain cytokines was hampered by the small quantities of the naturally occurring factors available from natural sources, e.g., blood and urine. Many of the cytokines have recently been molecularly cloned, heterologously expressed and purified to homogeneity. [D. Metcalf, "The Molecular Biology and Functions of the Granulocyte-Macrophage Colony Stimulating Factors," *Blood*, 67(2): 257–267 (1986).] Among these cytokines are gamma interferon, human and murine GM-CSF, human G-CSF, human CSF-1 and human and murine IL-3. Several of these purified factors have been found to demonstrate regulatory effects on the hematopoietic and immune systems in vivo, including GM-CSF, G-CSF, IL-3 and IL-2.

There remains a need in the art for additional proteins purified from their natural sources or otherwise produced in homogeneous form, which are capable of stimulating or enhancing immune responsiveness and are suitable for pharmaceutical use.

BRIEF SUMMARY OF THE INVENTION

In one aspect the present invention provides a novel human natural killer stimulatory factor, called NKSF, which is substantially free from other mammalian proteins. Active NKSF has an apparent molecular weight of approximately 70–80 kD. Pure preparations of NKSF reveal the presence of two polypeptides, subunits of approximately 40 kD and 30 kD, which, when associated, yield active NKSF. It is presently speculated that NKSF is a heterodimer formed by association of both the larger and smaller subunits through one or more disulfide bonds. This apparent heterodimeric structure can be generated by association of the two individual subunits.

The active, approximately 70–80 kD, NKSF is further characterized by containing all or a portion of the amino acid sequences of FIG. 1 and/or FIG. 2. Additionally, one or more of nine sequences of amino acids is present in the primary sequence of either the larger or smaller of the NKSF subunits. These nine amino acid fragments are listed and discussed in detail below.

The larger subunit polypeptide of NKSF is characterized by having an apparent molecular weight of 40 kD. This subunit is further characterized by having the same or substantially the same amino acid sequence as described in FIG. 1, containing the N-terminal sequence:

Ile-Trp-Glu-Leu-Lys-Lys-Asp-Val-Tyr-Val-Val-Glu-Leu-Asp-Trp-Tyr-Pro-Asp-Ala-Pro-Gly-Glu-Met. This N-terminal amino acid sequence corresponds to amino acids #23–45 of FIG. 1. This polypeptide is further characterized by containing six of the nine amino acid fragments.

The smaller polypeptide subunit of NKSF is characterized by an apparent molecular weight of approximately 30–35 kD. Two cDNA sequences have been identified for the smaller subunit. The shorter of the two sequences is substantially contained within the longer sequence in plasmid p35nksf14-1-1, illustrated in FIG. 2. The smaller subunit is further characterized by having the same or substantially the same amino acid sequence as described in FIG. 2, containing the following N-terminal sequence:

Arg-Asn-Leu-Pro-Val-Ala-Thr-Pro-Asp-Pro-Gly-Met-Phe-Pro. This fragment corresponds to underlined amino acids #57–70 of the p35nksf14-1-1 clone.

This smaller polypeptide is further characterized by containing three of the nine fragments of amino acids identified by underlining in FIG. 2.

NKSF displays biological activity in inducing the production of gamma interferon in vitro in human peripheral blood lymphocytes (PBLs). In homogeneous form, NKSF is characterized by a specific activity of greater than 1×10⁷ dilution units per milligram in the gamma interferon induction assay, described in detail below.

In addition to the induction of gamma interferon in PBLs, NKSF demonstrates the following biological activities:

(1) biological activity in a granulocyte-macrophage colony stimulating factor (GM-CSF) inducing assay with PBLs;

(2) biological activity in activating Natural Killer (NK) cells to kill leukemia and tumor-derived cells;

(3) biological activity in a tumor necrosis factor (TNF) inducing assay with phytohemagglutinin (PHA)-activated T lymphocytes;

(4) co-mitogenic activity with peripheral blood T lymphocytes; and (5) synergizes with IL-2 in inducing γ IFN production in PBLs and maintaining PBL proliferation.

Another aspect of the invention includes DNA sequences comprising cDNA sequences encoding the expression of a human NKSF polypeptide, a human NKSF larger subunit polypeptide, and a human NKSF smaller subunit polypeptide. Such sequences include a sequence of nucleotides encoding one or more of the subunits and peptide sequences described above.

Also provided by the present invention is a vector containing a DNA sequence encoding NKSF or a subunit of NKSF in operative association with an expression control sequence. Host cells transformed with such vectors for use in producing recombinant NKSF or its recombinant subunits are also provided by the present invention.

As still a further aspect of the present invention, there is provided recombinant NKSF protein. This protein is free from other mammalian proteinaceous materials and is characterized by the presence of a DNA sequence encoding one or more of the above-described subunits or peptide fragments containing one or more of the above-described physical, biochemical or biological activities or characteristics.

Another aspect of this invention provides pharmaceutical compositions containing a therapeutically effective amount of homogeneous or recombinant NKSF, or an effective amount of one or both of the subunits of NKSF, or of one or more of the peptide fragments thereof. These pharmaceutical compositions may be employed in methods for treating cancer, viral infections, such as AIDS, bacterial infections, and other disease states responsive to the enhanced presence of gamma interferon or GM-CSF production. Thus, generally this factor may be employed in the treatment of diseases in which stimulation of immune function might be beneficial.

A further aspect of the invention, therefore, is a method for treating cancer and/or other pathological states which may benefit from enhanced natural killer cell functions by administering to a patient a therapeutically effective amount of NKSF or one or both of its subunits or peptide fragments thereof in a suitable pharmaceutical carrier. These therapeutic methods may include administering simultaneously or sequentially with NKSF or one or more of its subunits or peptide fragments an effective amount of at least one other cytokine, hematopoietin, interleukin growth factor, or antibody. Specifically, the administration of NKSF or one or more of its subunits with IL-2 has demonstrated synergistic effects. Because of the synergy with IL-2 in vitro, this interleukin might be particularly effective in combination with NKSF.

Still a further aspect of the present invention is a process for producing homogeneous NKSF, or a subunit thereof from a human cell line producing NYSF or a subunit thereof in admixture with other proteins and polypeptides. This process of production provided by the present invention includes culturing selected cells capable of producing NKSF, its subunits, or peptide fragments thereof to obtain conditioned medium and purifying the conditioned medium through five primary purification steps.

The vectors and transformed cells of the invention are employed in another aspect, a novel process for producing recombinant human NKSF protein, a subunit thereof or peptide fragments thereof. In this process a cell line transformed with a DNA sequence encoding on expression NKSF protein, a subunit thereof or a peptide fragment thereof in operative association with an expression control sequence therefore is cultured. This claimed process may employ a number of known cells as host cells for expression of the polypeptide. Presently preferred cell lines are mammalian cell lines and bacterial cells.

Other aspects and advantages of the present invention will be apparent upon consideration of the following detailed description of preferred embodiments thereof.

BRIEF DESCRIPTION OF THE DRAWINGS

FIG. 1 is a nucleotide and amino acid sequence of the 40 kD subunit of NKSF.

FIG. 2 is a nucleotide and amino acid sequence of the 30 kD subunit of NKSF.

DETAILED DESCRIPTION OF THE INVENTION

The novel human natural killer cell stimulatory factor, NKSF, provided by the present invention is a homogeneous protein or proteinaceous composition substantially free of association with other mammalian proteinaceous materials.

Natural killer stimulatory factor has an apparent molecular weight of approximately 70–80 kD as determined by sodium dodecylsulfate polyacrylamide gel electrophoresis (SDS-PAGE) under non-reducing conditions. This 70–80 kD peptide is active in a gamma interferon induction assay.

Under reducing conditions in SDS-PAGE, the 70–80 kD band yields two smaller subunits with apparent molecular weights of approximately 40 kD (larger subunit) and approximately 30–35 kD (smaller subunit). For both subunits individually, the biological activity in the same gamma interferon induction assay is substantially lost compared to that of the native 70–80 kD species. The amino terminal sequences identified above were originally determined from the 40 kD reduced species and the 30–35 kD reduced species believed to be the subunits of the NKSF heterodimer. It is presently believed that NKSF is a disulfide-bonded heterodimer of the larger and smaller subunits. However, it is also possible that one or both of these subunits, when present alone, may have biological activity.

NKSF is, at least in part, an anionic glycoprotein. Under isoelectric focusing, two species of the NKSF are observed having isoelectric points of 4.3 and 4.8. It is presently speculated that the two species differ in glycosylation patterns.

NKSF is primarily characterized by biological activity in the gamma interferon induction assay described in detail in Example 8 below. Among its other biological activities include the ability to induce GM-CSF production by human peripheral blood lymphocytes. [See, e.g., published PCT application WO86/00639 for additional information on GM-CSF]. NKSF also has an enhancing effect on the mitogenic activity of various mitogens, such as lectins and phorbol diesters, on peripheral blood T lymphocytes and has a growth promoting effect on activated human tonsillar B cells. NKSF has also been observed to enhance NK cell functions to kill leukemia and tumor-derived cells in vitro. using a spontaneous cell cytotoxicity assay and an antibody dependent cell cytotoxicity (ADCC) assay.

In a spontaneous cell cytotoxicity assay, human peripheral blood lymphocytes or purified NK cells are incubated in the presence of NKSF for a period of 8 to 18 hours. Lymphocytes and NK cells are then assayed in a standard $^{51}$Cr-release assay for their ability to lyse target cells such as leukemia cell lines, tumor-derived cell lines, or virus-infected fibroblasts. NKSF dramatically increases the ability of NK cells to lyse such target cells at a level comparable to that obtained with interferon alpha and IL-2, well known activators of NK cell cytotoxic activity [See, e.g., G. Trinchieri et al, *J. Exp. Med.*, 147:1314 (1978) and G. Trinchieri et al, *J. Exp. Med.*, 160:1146 (1984)].

In an ADCC assay target cancer cells are coated with antibodies capable of binding to the Fc receptor on NK cells, e.g., $IgG_{2a}$, $IgG_3$ and the like. In preliminary assays, the presence of NKSF appears to enhance the killing activity of the NK cells for the coated tumor cells in ADCC. [See, e.g., L. M. Weiner et al, *Cancer Res.*, 48:2568–2573 (1988); P. Hersey et al, *Cancer Res.*, 46:6083–6090 (1988); and C. J. Hansik et al, *Proc. Natl. Acad. Sci.*, 83:7893–97 (1986) for additional information on ADCC.]

Preliminary analysis of NKSF in a B-cell growth factor assay using normal human B cells stimulated with goat anti-human IgM antibody (anti-µ) coupled to beads indicates that NKSF may also be characterized by B cell growth factor activity. In this assay the antibody directed against the IgM immunoglobulin on the surface of the B cell activates the B cell and causes it to become responsive to B cell growth factors. [See, C-T K. Tseng et al, *J. Immunol.*, 140:2305–2311 (1988)]. Such antibodies are commercially available.

NKSF was originally detected in the conditioned medium of the human cell line, RPMI 8866, a commercially available cell line [University of Pennsylvania Cell Center] which produces a mixture of lymphokines. This factor may also be produced by other Epstein Barr virus-transform ed lymphoblastoid cell lines or from other human cell lines. The RPMI 8866 cell line produces the factor spontaneously, but the level of production can be enhanced by treating the cell line with phorbol esters, such as phorbol dibutyrate. The cells deprived of serum for 48 hours still produce NKSF along with other lymphokines. Procedures for culturing RPMI 8866 (see Example 1) or another cell source of NKSF are known to those of skill in the art.

The purification technique employed in obtaining NKSF from cells which naturally produce it, uses the following steps. These steps include purification through an ion exchange column, e.g., QAE Zeta preparative cartridge [LKB Pharmacea], which indicates that the NKSF protein is anionic. The second purification step is a lentil lectin column which demonstrates that NKSF is, at least in part, a glycoprotein. The eluate from the lentil lectin column is further purified through a hydroxylapatite column, followed by a heparin sepharose column and a fast protein liquid chromatography (FPLC) Mono-Q column. The NKSF from RPMI 8866 eluted as a single peak in each of the three latter columns. A remaining protein contaminant of about 37 kD is removed by gel filtration chromatography alone or reverse phase HPLC and gel filtration chromatography. The resulting purified homogeneous NKSF was assayed for biological activity in the gamma interferon induction assay of Example 8 and demonstrated a specific activity of greater than $1 \times 10^7$ dilution units per milligram.

Thus, the homogeneous NKSF may be obtained by applying the above purification procedures, which are described in detail in Example 2 to the conditioned medium of RPMI 8866 or other sources of human NKSF.

NKSF, one or both of its subunits, or peptide fragments thereof may also be produced via recombinant techniques, e.g., by culturing under suitable conditions a host cell transfected with DNA sequences encoding the larger and/or smaller subunit in operative association with a regulatory control sequence capable of directing expression thereof.

The DNA sequences for cloned NKSF and its subunits were originally isolated by preparing tryptic digests of the homogeneous polypeptide. For example, the nine tryptic fragments originally found in NKSF are identified below:

Fragment 1: Leu-Thr-Ile-Gln-Val
Fragment 2: Lys-Tyr-Glu-Asn-Tyr-Thr
Fragment 3: Ile-Trp-Glu-Leu-Lys
Fragment 4: Leu-Met-Asp-Pro-Lys
Fragment 5: Val-Met-Ser-Tyr-Leu-Asn-Ala
Fragment 6: Ala-Val-Ser-Asn-Met-Leu-Gln-Lys
Fragment 7: Asn-Ala-Ser-Ile-Ser-Val
Fragment 8: Thr-Phe-Leu-Arg
Fragment 9: Asp-Ile-Ile-Lys-Pro-Asp-Pro-Pro-Lys.

Fragments 4, 5 and 6 have been identified as being located within the smaller or 30 kD subunit. These sequences correspond to the underlined amino acids #179–184, 246–252, and 81–86, respectively, of the p35nksf14-1-1 clone illustrated in FIG. 2. Fragments 1–3 and 7–9 have been identified as being located within the larger, 40 kD, NKSF subunit. Amino acid sequences corresponding to Fragment 1 (amino acids #75–79); Fragment 2 (amino acids #219–224); Fragment 3 (amino acids #23–27); Fragment 7 (amino acids #303–308); Fragment 8 (amino acids #127–130); and Fragment 9 (amino acids #231–239) are underlined in FIG. 1. Additionally, the amino terminal sequences of the larger and smaller subunits of NKSF were identified as described below in Example 5 and are underlined in FIG. 1 (#23–45) and FIG. 2 (#57–70), respectively.

Oligonucleotide probes were synthesized using the genetic code to predict all possible sequences that encode the amino acid sequences of these tryptic digestion products of NKSF. The same procedure may be followed by constructing probes from the above-identified amino terminal sequences of the two subunits of NKSF. The NKSF subunit genes can be identified by using these probes to screen a human genomic library. Alternatively, the mRNA from RPMI-8866 or another cell source of NKSF can be used to make a cDNA library which can be screened with the probes to identify the cDNAs encoding the polypeptides of the NKSF large and small subunits. Once the cDNAs were identified, they were introduced into an expression vector to make an expression system for NKSF, or one or both of its subunits.

By such use of recombinant techniques, DNA sequences encoding the polypeptides of the NKSF large and small subunit were obtained, which contain DNA sequences encoding the tryptic fragments or the amino terminal sequences identified above.

One NKSF clone, named pNK40-4, has the DNA and amino acid sequences presented in FIG. 1 below and codes for all or a portion of the larger NKSF subunit:

This cloned sequence in plasmid pNK40-4 was deposited with the American Type Culture Collection, 12301 Parklawn Drive, Rockville, Md. on Jul. 31, 1990 under accession number 40854. A prior partial clone of this larger fragment, containing the N-terminal non-coding region through sequence containing up to approximately nucleotide #888, was called pNK-6 and deposited with the ATCC on Feb. 3, 1989 under ATCC No. 40545. Another partial clone of the larger subunit, pNK162 was sequenced and contains the sequence from nucleotides #643 to 2362 of FIG. 1. This clone is maintained at the labs of Genetics Institute, Inc.

Two independent cDNA clones were identified which encode the sequence of the small (30–35 kD) subunit of NKSF. The longer clone (designated p35nksf14-1-1) is shown in FIG. 2. The shorter clone (designated p35nksf9-1-1) begins at nucleotide #133 (indicated by *) and ends at nucleotide #1335 (indicated by *) of FIG. 2 and the deposited sequence. Between those two nucleotides, the smaller clone is identical to the sequence of FIG. 2 except for 5 nucleotide changes in the 3' non-coding region. This shorter clone thus has a coding sequence beginning with Met (amino acid #35) in FIG. 2. The additional sequence at the 5' end of p35nksf14-1-1 encodes an in-frame initiation codon (ATG) 34 residues 5' of the operative initiation codon in p35nksf9-1-1.

Both of these clones encode all of the peptide sequences identified in the tryptic digest of purified NKSF, which were not found in the 40 kD subunit protein, as well as the amino terminal sequence of the purified 30 kD subunit. These sequences are underlined in FIG. 2. The clones contain the coding sequence for two possible versions of the 30–35 kD subunit of NKSF depending on whether translation begins with Met #1 or Met #35 in FIG. 2. However, because the 30–35 kD protein subunit of NKSF is believed to be generated by cleavage following Ala (amino acid #56), both sequences should yield the same mature protein. The sequence of p35nksf14-1-1 was deposited with the ATCC on Sep. 11, 1990 under accession number 40886.

Sequence from p35nksf9-1-1 (from the Pst I site underlined in FIG. 2 to the Pst I site in the Bluescript polylinker sequence), when introduced into Cos cells in the expression vector pEMC3(1) along with a plasmid expressing the 40 kD subunit, yielded biologically active NKSF. This material was active in the same bioassays used to test natural NKSF as discussed below. This sequence may be obtained from p35nksf14-1-1 by digestion with Pst I. Alternatively the cloned sequence of plasmid p35nksf9-1-1, containing the shorter 30–35 kD subunit sequence, is being maintained at the laboratories of Genetics Institute, Cambridge Park, Mass. and will be made available to the public upon grant of the patent.

A cDNA suitable for expression of the longer version of the 36–35 kD subunit may be obtained from the p35nksf14-1-1 deposited clone by digestion with SalT and NotI. The longer 30–35 kD subunit contains an earlier Met (amino acid #1) codon, additional 5' coding and non-coding sequences as well as 3' non-coding sequence. The sequence from Met (amino acid #35) to the N-terminus of the mature protein (encoded by both cDNAs). encodes a sequence which resembles a signal peptide and may direct the proper folding and/or secretion of the subunit. It is therefore possible that the longer 30–35 kD subunit sequence may be more efficiently expressed and secreted by the Cos cells than the shorter version. It may also fold differently, thereby conferring NKSF activity independent of the presence of the 40 kD subunit.

FIG. 2 indicates the placement of polylinker sequence in the deposited clone, as well as the first and last nucleotide of the larger and smaller versions of this subunit. Also indicated in the sequence are the 5' PstI site for obtaining the sequence of the small subunit which has been expressed and underlined tryptic fragment sequences.

Allelic variations of DNA sequences encoding the peptide sequences and the large and small subunits described above are also included in the present invention as well as analogs or derivatives thereof.

Thus the present invention also encompasses these novel DNA sequences, free of association with DNA sequences encoding other primate proteins, and coding on expression for NKSF polypeptides, including those of its large and small subunits. These DNA sequences include those containing one or more of the above-identified DNA and peptide sequences and those sequences which hybridize under stringent hybridization conditions [see, T. Maniatis et al, *Molecular Cloning* (*A Laboratory Manual*), Cold Spring Harbor Laboratory (1982), pages 387 to 389] to the DNA sequences. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C.

DNA sequences which hybridize to the sequences for NKSF or its subunits under relaxed hybridization conditions and which code on expression for NKSF peptides having NKSF biological properties also encode novel NKSF polypeptides. Examples of such non-stringent hybridization conditions are 4×SSC at 50° C. or hybridization with 30–40% formamide at 42° C. For example, a DNA sequence which shares regions of significant homology, e.g., sites of glycosylation or disulfide linkages, with the sequences of NKSF and encodes a protein having one or more NKSF biological properties clearly encodes a NKSF polypeptide even if such a DNA sequence would not stringently hybridize to the NKSF sequences.

Similarly, DNA sequences which code for NKSF polypeptides coded for by the sequence of NKSF, but which differ in codon sequence due to the degeneracies of the genetic code or allelic variations (naturally-occurring base changes in the species population which may or may not result in an amino acid change) are also encompassed by this invention. Variations in the DNA sequence of NKSF which are caused by point mutations or by induced modifications to enhance the activity, half-life or production of the polypeptides encoded thereby are also encompassed in the invention.

NKSF polypeptides may also be produced by known conventional chemical synthesis. Methods for constructing the polypeptides of the present invention by synthetic means are known to those of skill in the art. The synthetically-constructed NKSF polypeptide sequences, by virtue of sharing primary, secondary, or tertiary structural and conformational characteristics with NKSF polypeptides may possess NKSF biological properties in common therewith. Thus, they may be employed as biologically active or immunological substitutes for natural, purified NKSF polypeptides in therapeutic and immunological processes.

The NKSF polypeptides provided herein also include factors encoded by sequences similar to those of purified homogeneous and recombinant NKSF protein, or the subunit polypeptides, but into which modifications are naturally provided or deliberately engineered. Modifications in the peptides or DNA sequences can be made by one skilled in the art using known techniques. Modifications of interest in the NKSF sequences may include the replacement, insertion or deletion of a selected amino acid residue in the coding sequences. Mutagenic techniques for such replacement, insertion or deletion are well known to one skilled in the art. [See, e.g., U.S. Pat. No. 4,518,584.]

Other specific mutations of the sequences of the NKSF polypeptide or the subunit polypeptides described herein may involve modifications of a glycosylation site. The absence of glycosylation or only partial glycosylation results from amino acid substitution or deletion at any asparagine-linked glycosylation recognition site or at any site of the molecule that is modified by addition of O-linked carbohydrate. An asparagine-linked glycosylation recognition site comprises a tripeptide sequence which is specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

Expression of such altered nucleotide sequences produces variants which are not glycosylated at that site.

Other analogs and derivatives of the sequence of NKSF or of its subunits which would be expected to retain NKSF activity in whole or in part may also be easily made by one of skill in the art given the disclosures herein. One such modification may be the attachment of polyethylene glycol onto existing lysine residues or the insertion of a lysine residue into the sequence by conventional techniques to enable the attachment. Such modifications are believed to be encompassed by this invention.

The present invention also provides a method for producing NKSF polypeptides. The method of the present invention involves culturing a suitable cell or cell line, which has been transformed with a DNA sequence coding on expression for an NKSF polypeptide or subunit, under the control of known regulatory sequences. Preferably DNA sequences for both subunits are transformed into a host cell.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446. Expression of two different DNAs simultaneously in CHO cells has been described, for example, in published PCT International Application WO88/08035. Other suitable mammalian cell lines, are the monkey COS-1 cell line, and the CV-1 cell line, originally developed at the Wistar Institute, Philadelphia, Pa.

Similarly useful as host cells suitable for the present invention are bacterial cells. For example, the various strains of *E. coli* (e.g., HB101, MC1061 and strains used in the following examples) are well-known as host cells in the field of biotechnology. Various strains of *B. subtilis,* Pseudomonas, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering,* 8:277–298 (Plenum Press 1986) and references cited therein.

The present invention also provides vectors for use in the method of expression of novel NKSF polypeptides. These vectors contain the novel NKSF DNA sequences which code for NKSF polypeptides of the invention, including the subunit polypeptides. Alternatively, vectors incorporating modified sequences as described above are also embodiments of the present invention and useful in the production of NKSF polypeptides. The vector employed in the method also contains selected regulatory sequences in operative association with the DNA coding sequences of the invention and capable of directing the replication and expression thereof in selected host cells.

Thus NKSF, purified to homogeneity from cell sources or produced recombinantly or synthetically, may be used in a pharmaceutical preparation or formulation to treat cancer or other disease states which respond to enhanced NK cell activity or increased in vivo production of gamma interferon or GM-CSF. Such pathological states may result from disease, exposure to radiation or drugs, and include for example, leukopenia, bacterial and viral infections, anemia, B cell or T cell deficiencies including immune cell or hematopoietic cell deficiency following a bone marrow transplantation. Therapeutic treatment of cancer and other diseases with these NKSF polypeptide compositions may avoid undesirable side effects caused by treatment with presently available drugs. The NKSF polypeptide compositions according to the present invention may also be used in the treatment of Acquired Immunodeficiency Syndrome (AIDS) and other viral infections, particularly non-responsive viral infections, as well as bacterial infections.

It may also be possible to employ one or both of the subunit polypeptides of NKSF or peptide fragments thereof in such pharmaceutical formulations.

The polypeptides of the present invention may also be employed, alone or in combination with other cytokines, hematopoietins, interleukins, growth factors or antibodies in the treatment of cancer or other disease states. For example, NKSF polypeptides have been shown to have a synergistic effect when administered in connection with IL-2. This is expected to be useful in the treatment of infections, particularly viral infections and cancers. Other uses for these novel polypeptides are in the development of monoclonal and polyclonal antibodies generated by standard methods for diagnostic or therapeutic use.

Therefore, as yet another aspect of the invention are methods and therapeutic compositions for treating the conditions referred to above. Such compositions comprise a therapeutically effective amount of the NKSF protein or a subunit polypeptide or therapeutically effective fragment thereof of the present invention in admixture with a pharmaceutically acceptable carrier. This composition can be systemically administered parenterally. Alternatively, the composition may be administered intravenously. If desirable, the composition may be administered subcutaneously. When systematically administered, the therapeutic composition for use in this invention is in the form of a pyrogen-free, parenterally acceptable aqueous solution. The preparation of such a pharmaceutically acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 1–1000 micrograms of NKSF protein or subunit thereof or 50 to 5000 units (i.e., one unit per ml being the concentration of protein which leads to half maximal stimulation in the gamma interferon induction assay) of protein per kilogram of body weight.

The therapeutic method and compositions of the present invention may also include co-administration with other human factors. Exemplary cytokines or hematopoietins for such use include the known factors IL-1, IL-2 and IL-6 particularly. [See, e.g., PCT publications WO85/05124, and WO88/00206; and European patent application 0,188,864.] Other potential candidates for participation in NKSF therapymay also include IL-4, G-CSF, CSF-1, GM-CSF, IL-3, IL-11 or erythropoietin. Growth factors like B cell growth factor, B cell differentiation factor, or eosinophil differentiation factors may also prove useful in co-administration with NKSF.

Similarly, administration of NKSF or a subunit or fragment thereof with or prior to administration of an antibody capable of binding to the Fc receptor on NK cells may enhance ADCC therapy directed against tumors. The dosage recited above would be adjusted to compensate for such additional components in the therapeutic composition. Progress of the treated patient can be monitored by conventional methods.

The following examples illustratively describe the purification and characteristics of homogeneous human NKSF and other methods and products of the present invention. These examples are for illustration and do not limit the scope of the present invention.

EXAMPLE 1
Preparation of Serum-Free RPMI 8866 Cell-Conditioned Medium

The human B-lymphoblastoid cell line RPMI 8866 was maintained in RPMI 1640 medium containing 5% heat-inactivated fetal calf serum (FCS). For preparation of serum free conditioned medium, cells were washed and suspended ($10^6$ cells/ml) in serum free RPMI 1640 medium containing $10^{-7}$ M phorbol-12-13-dibutyrate (PdBU) and cultured for 48 hours at 37° C., 5% $CO_2$. The cell free supernatants were harvested by filtration through a 0.2 μm filter [Durapore® hydrophilic cartridge filter, Millipore, Bedford, Mass.], and Tween-20 and phenylmethylsulfonyl-fluoride (PMSF) were added to 0.02% and 0.1 mM, respectively. The cell conditioned medium was then concentrated 50 fold under pressure using an ultra-filtration cartridge [Spiral-Wound, S1, Amicon, Danvers, Mass.].

EXAMPLE 2
Purification of NKSF from Conditioned Medium

The following procedures are presently employed to obtain homogeneous NKSF protein from RPMI 8866 conditioned medium, as described in Example 1 above.

a. Anion Exchange Cartridge Chromatography

Two liters of the crude concentrated conditioned medium was diluted with distilled water to a conductivity of 6 m Os/cm and adjusted to pH 8 with 1 M Tris-HCl buffer (pH 8). The concentrate was then applied to five QAE Zetaprep 250 cartridges [Phannacia] connected in parallel and previously equilibrated with 0.1 M Tris-HCl buffer (pH 8) at a flow rate of 150 ml/min. Unless otherwise cited, all the buffers used for purification contained 0.02% Tween-20 and 0.1 mM PMSF. The cartridges were washed with 3 liters of 0.1 M Tris-HCl buffer (pH 6.8) followed by washing with 1.5 liters of 0.5 M NaCl in 0.1 M Tris-HCl buffer (pH 6.8) and 300 ml fractions were collected. The NKSF activity was eluted with the 0.5 M NaCl-containing wash.

b. Lentil-Lectin Sepharose Chromatography

Pooled NKSF-containing fractions from two separate QAE Zetaprep elutions were pooled and applied directly to a column (2.5×15 cm) of lentil-lectin Sepharose 4B [Pharmacia] which has been equilibrated with 20 mM Tris-HCl buffer (pH 7.2). After washing with five column volumes of equilibration buffer, the column was eluted with three column volumes of 20 mM Tris-HCl buffer (pH 7.2) containing 0.2 M α-methyl-D-mannopyranoside [Sigma] and 0.5 M NaCl. Approximately half of the NKSF activity was bound by the column and was recovered in the fractions eluted with α-methyl-D-mannopyranoside.

c. Hydroxylapatite Chromatography

Concentrated material from the pool of NKSF activity which bound to the lentil-lectin Sepharose column was dialyzed against 1 mM potassium phosphate buffer (pH 6.8) containing 0.1 mM $CaCl_2$ and 0.15 M NaCl and applied to a Biogel HT [BioRad] column (2×5 cm) previously equilibrated with 1 mM potassium phosphate buffer (pH 6.8) containing 0.1 mM $CaCl_2$. The column was washed with five column volumes of equilibration buffer and eluted with 100 ml of a linear gradient from 1 mM to 400 mM potassium phosphate buffer (pH 6.8) containing 0.15 M NaCl. 4 ml fractions were collected and tested for NKSF activity. A single peak of activity emerged from the column between the approximately 200 mM and 300 mM potassium phosphate.

d. Heparin-Sepharose Chromatography

Eluted NKSF-containing fractions from the Biogel HT column were pooled and dialyzed against 20 mM sodium phosphate buffer (pH 7.2) and applied to a Heparin Sepharose [Pierce, Rockford, Ill.] column (1×10 cm). The column was washed with five column volumes of 20 mM sodium phosphate buffer (pH 7.2) and eluted with the same buffer containing 1 M NaCl. 3 ml fractions were collected and NKSF activity measured. Essentially all of the activity was bound by the Heparin column and recovered in the 1 M NaCl wash.

e. Mono Q Chromatography

Pooled fractions from the Heparin Sepharose column were dialyzed against 20 mM Tris-HCl buffer (pH 6.8) containing 1% ethylene glycol and 0.1 mM PMSF but no Tween-20 (buffer A) and concentrated to 2 ml using a stirred cell [Amicon] with a YM 10 membrane. The sample was applied to a Mono Q (5/5) column [Pharmacia-FPLC apparatus] and eluted with a linear gradient from 0 M to 1 M NaCl in buffer A (pH 6.8). 0.5 ml fractions were collected and tested for NKSF activity. The activity emerged from the column as a single peak between approximately 220 mM and 270 mM NaCl.

f. Gel Filtration Chromatography

Pooled fractions containing NKSF activity from the Mono Q column were concentrated to 100 microliters by Speedvac Concentrator [Savant, Farmingdale, N.Y.] and applied to a FPLC Superose 12 column. Chromatography was run with 50 mM sodium phosphate buffer (pH 7.2) containing 0.15 M NaCl, 1% ethylene glycol and 0.1 mM PMSF. Flow rate was 0.6 ml/minute and 0.5 ml fractions were collected. NKSF protein (70 kD) was separated from the approximately 37 kD protein contaminant.

Alternatively, the pooled Mono-Q fractions may be subjected to reverse-phase HPLC (C8 column) prior to the step (f) described above, to separate the protein contaminant from the active 70 kD protein.

EXAMPLE 3
Sodium Dodecyl Sulfate-Polyacrylamide Gel Electrophoresis

SDS-PAGE was performed according to the method of Laemmli [Laemmli, U. K., *Nature*, 227:680–685 (1970)] on 10% acrylamide slab gels (0.75 mm thickness). After electrophoresis the gels were either stained by the silver-nitrate method using a silver staining reagents [BioRad] or cut into 2 mm slices and eluted in 0.5 ml RPMI medium for 4 hours at 24° C. and assayed for NKSF activity. Apparent molecular weight was determined with protein standards, phospholipase b (94 kD), bovine serum albumin (67 kD), ovalbumin (43 kD), carbonic anhydrase (30 kD), soybean trypsin inhibitor (20 kD) and lactalbumin (14.4 kD).

SDS-PAGE analysis (non-reducing conditions) of the Mono Q column fractions (Example 2, step (e)) beginning with several fractions which eluted before the NKSF activity, continuing right through the active fractions and ending with fractions which eluted after the peak of NKSF activity, revealed that the presence of two proteins (70 kD and 37 kD) correlated with the presence of NKSF activity in the various Mono Q fractions. The active fractions were rerun on a second non-reducing gel and the proteins were eluted from the regions corresponding to the 70 kD and 37 kD bands and tested for NKSF activity. The activity all correlated with the 70 kD species indicating that this protein is NKSF.

The 70 kD species was eluted from the gel, iodinated using chloramine T [Sigma, St. Louis, Mo.] and rerun on a second SDS gel after boiling for two minutes in the presence of the reducing agent, β-mercaptoethanol (10%). Under these conditions, the 70 kD species resolved into two distinct subunits of molecular weights 40 kD and 30 kD, indicating that the native NKSF may be a disulfide-bonded heterodimer of these subunit polypeptides. Alternatively, NKSF may be a dimer formed by multiples of the larger or smaller subunits. The reduction of the native 70 kD NKSF appeared to destroy all of its ability to induce peripheral blood lymphocyte production of gamma interferon.

EXAMPLE 4

Recovery of Protein

Starting with 500 liters of RPMI 8866 cell-free conditioned medium, the final pooled active fractions from the Mono Q column contained approximately 10 µg of protein, estimated from the intensities of silver staining by control proteins analyzed in parallel on the same gel. Approximately 6 µg of this corresponded to the 70 kD NKSF protein. The estimated specific activity of the 70 kD NKSF is $1 \times 10^7$ u/mg. The overall recovery of NKSF activity in the preparation was 2%.

EXAMPLE 5

NKSF Protein Composition

Homogeneous NKSF is reduced as described in the SDS-PAGE example above and digested with trypsin. Alternatively, non-reduced NKSF may be obtained from a reverse-phase HPLC column and digested with trypsin. Nine tryptic fragments are isolated having the following amino acid sequences:

Fragment 1—Leu-Thr-Ile-Gln-Val
Fragment 2—Lys-Tyr-Glu-Asn-Tyr-Thr
Fragment 3—Ile-Trp-Glu-Leu-Lys
Fragment 4—Leu-Met-Asp-Pro-Lys
Fragment 5—Val-Met-Ser-Tyr-Leu-Asn-Ala
Fragment 6—Ala-Val-Ser-Asn-Met-Leu-Gln-Lys
Fragment 7—Asn-Ala-Ser-Ile-Ser-Val
Fragment 8—Thr-Phe-Leu-Arg
Fragment 9—Asp-Ile-Ile-Lys-Pro-Asp-Pro-Pro-Lys.

Additionally, the amino acid sequences of the amino termini of each subunit of NKSF were determined from the isolated 40 kD and 30 kD species of NKSF after reduction, as described in Example 3. The amino terminal sequence from the 40 kD subunit was as follows: Ile-Trp-Glu-Leu-Lys-Lys-Asp-Val-Tyr-Val-Val-Glu-Leu-Asp-Trp-Tyr-Pro-Asp-Ala-Pro-Gly-Glu-Met. The amino terminal sequence above as well as Fragments 1–3 and 7–9 proved to be derived from the amino acid sequence of the clone of larger subunit identified in FIG. 1.

The amino terminal sequence from the 30 kD smaller subunit was as follows: Arg-Asn-Leu-Pro-Val-Ala-Thr-Pro-Asp-Pro-Gly-Met-Phe-Pro. Fragments 4, 5 and 6 proved to be derived from the amino acid sequence of the clone of the smaller subunit identified in FIG. 2.

Probes consisting of pools of oligonucleotides or unique oligonucleotides are designed according to the method of R. Lathe, *J. Mol. Biol.,* 183(1):1–12 (1985). The oligonucleotide probes are synthesized on an automated DNA synthesizer.

Because the genetic code is degenerate (more than one codon can code for the same amino acid) a mixture of oligonucleotides must be synthesized that contains all possible nucleotide sequences encoding the amino acid sequence of the tryptic fragment. It may be possible in some cases to reduce the number of oligonucleotides in the probe mixture based on codon usage because some codons are rarely used in eukaryotic genes, and because of the relative infrequency of the dinucleotide CpG in eukaryotic coding sequences [see J. J. Toole et al, *Nature,* 312:342–347 (1984)]. The regions of the amino acid sequences used for probe design are chosen by avoiding highly degenerate codons where possible. The oligonucleotides are synthesized on an automated DNA synthesizer and the probes are then radioactively labelled with polynucleotide kinase and $^{32}$P-ATP.

A cDNA encoding the small subunit of NKSF was identified by screening a cDNA library (prepared in lambda Zap; Stratagene cloning systems, La Jolla, Calif.) made from polyadenylated RNA from PdBu induced 8866 cells (Univ. of Pennsylvania Cell Center) using established techniques (see Toole et al cited above). The screening was carried out using oligonucleotides with sequence predicted by those tryptic peptides not contained within the previously cloned cDNA coding for the 40 kD protein as probes. Recombinants from this library are plated and duplicate nitrocellulose replicas made of the plates. The oligonucleotides are kinased with $^{32}$P gamma ATP and hybridized to the replicas.

In particular two pools of oligonucleotides were synthesized based on the peptide Val-Met-Ser-Tyr-Leu-Asn-Ala. The sequences in one pool of 17 mers were derived from the peptide sequence Met-Ser-Tyr-Leu-Asn-Ala and those in the second from Val-Met-Ser-Tyr-Leu-Asn. Clones which hybridized to the first pool of oligonucleotides were hybridized with the second pool. Hybridizations were performed at 48° C. in a buffer containing 3M TMAC. Filters were subsequently washed in 3M TMAC, 50 mM Tris pH 8 at 50° C. [See K. A. Jacobs et al, *Nucl. Acids Res.,* 16:4637–4650 (1988).] Duplicate positives were plaque purified. Two clones were identified which hybridized to both pools, p35nksf9-1-1, and p35nksf14-1-1, described above.

The sequence and computer translations of cDNA clone p35nksf14-1-1 is shown in FIG. 2. It includes all the peptide sequences identified in tryptic digests of purified NKSF not found in the 40 kD subunit protein (underlined) as well as the amino terminal sequence of the purified 30 kD subunit (underlined).

To obtain a full length cDNA clone for the 40 kD subunit of NKSF, cDNA that had been previously prepared from 8866 polyadenylated RNA was cloned into λZAP as described above. Two hundred thousand recombinants from this library were plated, duplicate nitrocellulose filters were prepared and screened with a random primed $^{32}$P labeled DNA fragment, the sequence of which is within pNK-6. The probing was done using standard stringent hybridization and washing conditions. Three duplicate positive plaques resulted from this screen. The plaques were replated and reprobed using the above probe and conditions to clonally isolate the plaques. The three isolates were then probed with a $^{32}$P end-labeled oligo dT probe (pd(T)$_{12-18}$, Pharmacia). This hybridization was done in 6×SSC, 5× Denhardt's solution, and carrier DNA plus labeled probe at room temperature. One of the three isolates, pNK162, hybridized to the oligo dT probe and was sequenced.

Using standard restriction digestion and subcloning techniques, NKSF clones pNK-6 and pNK162 were subcloned together in frame for transcription and translation and ligated into the pXM expression vector for COS expression. The resultant clone, pNK40-4 (FIG. 1) is believed to contain the full length cDNA for the 40 kD NKSF subunit.

EXAMPLE 6

Expression of Recombinant Human NKSF

To produce NKSF, the DNAs encoding its subunits are transferred into appropriate expression vectors, of which numerous types are known in the art for mammalian, insect, yeast, fungal and bacterial expression, by standard molecular biology techniques. One such vector for mammalian cells is pXM [Y. C. Yang et al, Cell, 47:3–10 (1986)]. This vector contains the SV40 origin of replication and enhancer, the adenovirus major late promoter, a cDNA copy of the adenovirus tripartite leader sequence, a small hybrid intervening sequence, an SV40 polyadenylation signal and the adenovirus VA I gene, in appropriate relationships to direct the high level expression of the desired cDNA in mammalian cells [See, e.g., Kaufman, Proc. Natl. Acad. Sci. USA, 82:689–693. (1985)]. The pXM vector is linearized with the endonuclease enzyme XhoI and subsequently ligated in equimolar amount separately to the cDNA encoding the NKSF subunits that were previously modified by addition of synthetic oligonucleotides [Collaborative Research, Lexington, Mass.] that generate Xho I complementary ends to generate constructs for expression of each subunit of NKSF.

Another vector for mammalian expression, pEMC3 (1) can be made by simple modification of the pEMC2B1 vector, described below. pEMC3 (1) differs from pEMC2B1 by three restriction sites, SmaI, SalI, XbaI, in the polylinker region. To make pEMC3(1), these three restriction sites are inserted between the PstI and EcoRI restriction sites of pEMC2B1 by conventional means.

pEMC2B1 may be derived from pMT2pc which has been deposited with the American Type Culture Collection (ATCC), Rockville, Md. (USA) under Accession Number ATCC 40348. The DNA is linearized by digestion of the plasmid with PstI. The DNA is then blunted using $T_4$ DNA polymerase. An oligonucleatide 5' TGCAGGCGAGCCT-GAATTCCTCGA 3' is then ligated into the DNA, recreating the PstI site at the 5' end and adding an EcoRI site and XhoI site before the ATG of the DHFR cDNA. This plasmid is called pMT21. pMT21 is cut with EcoRI and XhoI which cleaves the plasmid at two adjacent cloning sites. An EMCV fragment of 508 base pairs was cut from $pMT_2ECAT_1$ [S. K. Jong et al, J. Virol., 63:1651–1660 (1989)] with the restriction enzymes EcoRI and TaqαI. A pair of oligonucleotides 68 nuclectides in length were synthesized to duplicate the EMCV sequence up to the ATG. The ATG was changed to an ATT, and a C is added, creating a XhoI site at the 3' end. A TaqαI site is situated at the 5' end. The sequences of the oligonucleotides were: 5' CGAGGT-TAAAAAACGTCTAGGCCCCCCGAAC-CACGGGGACGTGGTTTTCCTTTGAAAAA-CACGATTGC 3' and its complementary strand.

Ligation of the pMT21 EcoRI-to-XhoI fragment to the EMCV EcoRI-to-TaqαI fragment and to the TaqαI/XhoI oligonucleotides produced the vector pEMC2B 1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The two different cDNAs are expressed simultaneously in the same host or independently in different hosts. In the latter case, the subunits are purified separately and the final active NKSF is assembled by renaturation of the individual subunits.

a. Mammalian Cell Expression

To obtain expression of the NKSF protein for use in the assays described below, the constructs containing the cDNAs for the 40 kD and 30 kD (smaller version) subunits were cloned separately into the mammalian expression vector pEMC3(1) and together introduced into COS cells by calcium phosphate coprecipitation and transfection. $^{35}$S methionine labelled proteins (4 hr pulse, 2 days after transfection) of approximately 80 kD (nonreduced) and 40 kD and 30 kD (reduced) are present in PAGE gels of COS cotransfectant conditioned medium but not in negative control transfectants. The conditioned media from the COS cotransfectants collected 48 hrs after transfection, was active in the gamma interferon (IFNγ) induction assay (see Example 7a).

Further evidence that the activity was identical to that purified from 8866 conditioned medium comes from the observations that the cotransfected conditioned media synergizes with IL2 in the IFNγ induction assay and that polyclonal rabbit antiserum (1:100 dilution) to the NKSF heavy chain, blocks the activity in the cotransfectant as well as RPMI 8861 conditioned medium. The antiserum was produced by immunizing rabbits with NKSF heavy chain purified from conditioned media from COS cells transfected with the NKSF heavy chain cDNA (cloned in pEMC 3(1)).

When the pNK40-4 plasmid was separately transfected into COS cells, the supernatant was collected and assayed, and the cells pulse labeled with $^{35}$S cysteine. The labeled protein was run on an 11% acrylamide gel under standard reducing and nonreducing conditions. The unlabeled supernatant from this transfection with pNK40-4 was inactive in the gamma interferon induction assay and in the cell cytotoxicity assay, which were performed as described below in Example 8.

The mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, J. Mol. Biol., 159:511–521 (1982); and Kaufman, Proc. Natl. Acad. Sci., USA 82:689–693 (1985). Exemplary mammalian host cells include particularly primate cell lines and rodent cell lines, including transformed cell lines. Normal diploid cells, cell strains derived from in vitro culture of primary tissue, as well as primary explants, are also suitable. Candidate cells need not be genotypically deficient in the selection gene so long as the selection gene is dominantly acting. For stable integration of the vector DNAs, and for subsequent amplification of the integrated vector DNAs, both by conventional methods, CHO cells may be employed. Alternatively, the vector DNA may include all or part of the bovine papilloma virus genome [Lusky et al, Cell, 36:391–401 (1984)] and be carried in cell lines such as C127 mouse cells as a stable episomal element. Other suitable mammalian cell lines include but are not limited to, HeLa, COS-1 monkey cells, mouse L-929 cells, 3T3 lines derived from Swiss, Balb-c or NIH mice, BHK or HaK hamster cell lines.

Where the two subunits require simultaneous expression in mammalian cells, the two cDNAs may be introduced into the cells using two different selectable genes or markers. As discussed below in Example 7, this can readily be achieved in CHO cells using the dihydrofolate reductase (DHFR) gene as one marker and adenosine deaminase (ADA) as the other marker. Any combination of two genes which can be independently selected in any mammalian cell line are useful for this purpose. For example, a CHO cell line is independently developed for expression of one subunit under ADA selection and a different cell line is developed for expression of the other subunit under DHFR selection. The cell lines are fused in polyethylene glycol under double selection to yield stable lines expressing both subunits. Alternatively, the DNAs are introduced simultaneously or sequentially into the same cells, thereby yielding lines expressing active NKSF.

It is also possible that multicistronic vectors encoding both subunits with a single selectable marker might yield cells in which both subunits can be coamplified with one selective drug. Additionally, this effect may be achieved by simple cotransfection of cells simultaneously with separate vectors.

Stable transformants are then screened for expression of the product by standard immunological, biological or enzymatic assays. The presence of the DNA and mRNA encoding the NKSF polypeptides may be detected by standard procedures such as Southern blotting and RNA blotting. Transient expression of the DNA encoding the polypeptides during the several days after introduction of the expression vector DNA into suitable host cells, such as COS-1 monkey cells, is measured without selection by activity or immunologic assay of the proteins in the culture medium.

One skilled in the art can also construct other mammalian expression vectors comparable to the pEMC3 (1) vector by, e.g., inserting the DNA sequences of the NKSF subunits from the respective plasmids with appropriate enzymes and employing well-known recombinant genetic engineering techniques and other known vectors, such as pXM, pJL3 and pJL4 [Gough et al., *EMBO J.*, 4:645–653 (1985)] and pMT2 (starting with pMT2-VWF, ATCC #67122; see PCT application PCT/US87/00033). The transformation into appropriate host cells of these vectors with both NKSF subunits (either as separate vectors or in the same vector) can result in expression of the NKSF polypeptides.

b. Bacterial Expression Systems

Similarly, one skilled in the art could manipulate the sequences encoding the NKSF subunits by eliminating any mammalian regulatory sequences flanking the coding sequences and inserting bacterial regulatory sequences to create bacterial vectors for intracellular or extracellular expression of the NKSF subunits of the invention by bacterial cells. The DNA encoding the NKSF polypeptides may be further modified to contain different codons to optimize bacterial expression as is known in the art. Preferably the sequences encoding the mature NKSF subunits are operatively linked in-frame to nucleotide sequences encoding a secretory leader polypeptide permitting bacterial expression, secretion and processing of the mature NKSF polypeptides, also by methods known in the art. The simultaneous expression of both subunits of NKSF in *E. coli* using such secretion systems is expected to result in the secretion of the active heterodimer. This approach has yielded active chimeric antibody fragments [See, e.g., Bitter et al, *Science*, 240:1041–1043 (1988)].

Alternatively, the individual subunits are expressed in the mature form separately from the two different cDNAs in *E. coli* using vectors for intracellular expression and the subunits are isolated separately, mixed and refolded by procedures well known in the art. See, for example, U.S. Pat. No. 4,512,922. The compounds expressed through either route in bacterial host cells may then be recovered, purified, and/or characterized with respect to physicochemical, biochemical and/or clinical parameters, all by known methods.

c. Insect or Yeast Cell Expression

Similar manipulations can be performed for the construction of an insect vector for expression of NKSF polypeptides in insect cells [See, e.g., procedures described in published European patent application 155,476]. If the NKSF subunits are derived from a single cDNA, this cDNA will be expressed in insect cells. Alternatively, if the NKSF subunits are derived from two different cDNAs, each subunit is separately inserted into an insect cell vector and the two resulting vectors co-introduced into insect cells to express biologically active NKSF.

Similarly yeast vectors are constructed employing yeast regulatory sequences to express either the individual NKSF subunits simultaneously, or, if the protein is derived from a single precursor, the cDNA encoding that precursor, in yeast cells to yield secreted extracellular active NKSF heterodimer. Alternatively the individual subunits may be expressed intracellularly in yeast, the individual polypeptides isolated and finally, refolded together to yield active NKSF. [See, e.g., procedures described in published PCT application WO 86/00639 and European patent application EP 123,289.]

EXAMPLE 7

Construction of CHO Cell Lines Expressing High Levels of NKSF

One method for producing high levels of the NKSF protein of the invention from mammalian cells involves the construction of cells containing multiple copies of the two cDNAs encoding the individual NKSF subunits.

Because the two NKSF polypeptides are each derived from separate mRNAs, each corresponding cDNA must be expressed simultaneously in CHO cells. Two different selectable markers, e.g., DHFR and ADA, may be employed. One of the cDNAs is expressed using the DHFR system [Kaufman and Sharp, *J. Mol. Biol.*, (1982) supra.] using, e.g., the vector pEMC3 (1) to express one of the NKSF subunits and DHFR. The second subunit is expressed using a second vector, e.g. pMT3SV2ADA [R. J. Kaufman, *Meth. Enzymol.*, 185:537–566 (1990)]. Plasmid pMT3SV2ADA also directs the expression of ADA in mammalian cells. The first vector construct containing one subunit is transfected into DHFR-deficient CHO DUKX-BII cells. The second vector construct containing the second subunit is transfected into a second CHO cell line. The transfected cells are selected for growth in increasing concentrations of methotrexate beginning with approximately 5 nM with subsequent step-wise increments up to 100 $\mu$M for the DHFR marker, or in 2'-deoxycoformycin (dCF) for the ADA marker beginning with 100 nM with subsequent step-wise increments up to 10 $\mu$M. The expression of the individual cDNAs (one subunit under DHFR selection in one cell line and the other subunit under ADA selection in a second cell line) is assayed through a combination of mRNA blotting to test for transcription and immunoanalysis to test for protein production. The cells which express one of the subunits under ADA selection and the cells which express the other subunit under DHFR selection are finally fused in polyethylene glycol using methods well established in the art to yield a single cell line, resistant to both dCF and MTX and expressing both subunits to yield biologically active NKSF.

Another presently preferred method of expression is based on the development of a single cell line expressing both subunits. A first vector containing one subunit, e.g., the first vector described above, is transfected into a selected CHO cell line and the expression of the subunit is amplified under drug selection as described above. Thereafter the second vector containing the other subunit is transfected into the cell line which already contains amplified first vector. The cDNA expressing the other subunit, e.g., the second vector described above, may be introduced under a second drug selection. The second vector is then amplified by the same techniques, resulting in a single cell line expressing both subunits simultaneously. (See, e.g., published PCT International Application WO88/08035 for an exemplary description of independently amplifying a first gene linked to a DHFR gene and a second gene linked to an ADA gene.)

In another method, two.vectors constructs may be designed, e.g., a pEMC3(1) construct containing one subunit and the DHFR gene and a second pEMC3 (1) construct containing the second subunit and the DHFR gene. The two pEMC3 (1) constructs expressing both NKSF subunits may be mixed and the mixture transfected into CHO cells. The cells are then amplified in MTX as described above to obtain a cell line producing both subunits. Alternatively two drug markers may be employed in this method and the combined selection of both drugs may be used and transformants tested for NKSF activity directly to obtain cell lines expressing the heterodimer.

Still a further alternative is the development of a multi-cistronic vector encoding both subunits and one drug selection marker. Transfection of this vector and its amplification might more rapidly yield high expressing cell lines.

In any of the expression systems described above, the resulting cell lines can be further amplified by appropriate drug selection, resulting cell lines recloned and the level of expression assessed using the gamma interferon induction assay described herein.

EXAMPLE 8
Biological Activities of Human NKSF

The following assays were performed using either the homogeneous NKSF described in Example 2 or a partially purified version of NKSF. The recombinant version of the molecule is expected to exhibit NKSF biological properties in these same assays or other assays.

When fresh human peripheral blood mononuclear cells (PBMC) or phytohemagglutinin (PHA)-induced blasts are cultured with NKSF, significant amounts of gamma interferon are detected in the supernatant. Moreover, NKSF synergizes with IL-2, phorbol dibutyrate (PdBu), and PHA in inducing gamma interferon production. Northern blot analyses show that NKSF, alone or in combination with other factors, induces accumulation of gamma interferon mRNA. Gamma interferon message was found in both purified T and NK populations. Preincubation with the protein synthesis inhibitor, cycloheximide (CHX), leads to a superinduction of gamma interferon mRNA following stimulation with NKSF. HLA-DR(+) accessory cells are required for gamma interferon production by T and NK cells; Induction of gamma interferon mRNA can be detected as early as 1 hour after treatment with NKSF of PHA blasts. The details of the assay are described below.

a. Gamma Interferon Induction Assay

NKSF activity was measured by the induction of gamma interferon (gamma-IFN) expression in cultures of human peripheral blood lymphocytes (PBLs). In the assay, 100 μl of human PBLs suspended ($10^7$ cells/ml) in RPMI 1640 culture medium supplemented with 10% heat-inactivated FCS was added to 100 μl of sample to be tested in a microtiter plate [U-bottom, 96-well, Costar, Cambridge, Mass.] and incubated for 18 hours at 37° C., 5% $CO_2$. Samples to be tested included purified NKSF, dialyzed cell free supernatant from 48 hour phorbol diester stimulated RPMI 8866 cells, and recombinant IL-2 [Genetics Institute, Inc., PCT application WO85/05124]. After incubation, 100 μl of cell free supernatant was withdrawn from each well and the level of gamma-IFN produced measured by radioimmunoassay [Centocor Gamma Interferon Radioimmunoassay, Centocor, Malvern, Pa.]. One unit of NKSF per ml is the concentration required to produce one-half of the maximal gamma-IFN produced in the presence of optimal concentrations of NKSF.

There was a linear positive correlation between the amount of gamma-IFN produced in each well to the amount of NKSF in culture.

In addition to gamma-FN, NKSF induces T and NY cells to produce GM-CSF and tumor necrosis factor. The assay of production of these cytokines is performed as above and the supernatant is assayed for the presence of the cytokines by specific biological assays or by radioimmunoassays [Cuturi et al, J. Exp. Med., 165:1581–1594 (1987)]. Alternatively, the induction of the cytokine genes is measured by evaluating the accumulation of mRNA transcripts of the three cytokines in the lymphocytes treated with NKSF. Lymphocytes are cultured for 4 to 18 hours with NKSF, RNA is extracted by established methods, fractionated by agarose gel electrophoresis, blotted on nitrocellulose, and hybridized with $^{32}$P-labeled cDNA probes for the IFN-gamma, GM-CSF, or tumor necrosis factor genes (Northern blotting). Extent of hybridization is determined by autoradiography and densitometry.

NKSF induces production of IFN-gamma and TNF from purified human NK cells. When assayed as described under the gamma interferon induction assay of part (a) above, NK cells are able to lyse various target cells by two mechanisms. One mechanism is spontaneous lysis, in the absence of specific sensitization, of a variety of target cells, including leukemia- and solid tumor-derived cell lines, virus-infected cells, and, in some cases, normal cell lines. The second mechanism is ADCC. Preliminary evidence indicates that NKSF may enhance the ability of NK cells to lyse more efficiently target cells coated with IgG antibodies with an Fc portion able to bind to the NK cell Fc receptor.

b. NK Assay

In order to assay for the enhancement of NK cell spontaneous cytotoxicity by NKSF, PBLs or purified NK cells ($5 \times 10^6$ cells/ml) are incubated for 18 hours in RPMI 1640 medium, 10% heat inactivated FCS, in the presence of various dilutions of NKSF. PBLs are then washed and added, at PBL-target cells ratio from 1:1 to 100:1, to $10^4$ $_{51}$Cr-labeled target cells in a U-bottomed microtiter plate (final volume 200 μl). After 4 hours, the plates are centrifuged, the cell-free supernatant is collected and lysis of target cells is evaluated by the release of the $^{51}$Cr-label from the cells. NKSF increases several-fold the cytotoxicity of NK cells when assayed against the following target cells: malignant hematopoietic cell lines (i.e. K562, Daudi, U937, HL-60, ML3, Molt 4, Jurkat, THP-1), solid tumor-derived cell line (rhabdomyosarcoma, melanoma), and normal foreskin-derived fibroblast strains. The enhancement of NK cell-mediated cytotoxicity by NKSF is not secondary to the production of IFN-gamma, tumor necrosis factor, or IL-2, produced by the PBL treated with NKSF. The cytotoxic assay, the methods for NK cell purification, and for the quantitative evaluation of enhancement of NK cell-mediated enhancement by cytokines are described in detail in G. Trinchieri et al, J. Exp. Med., 147:1314 (1978); G. Trinchieri et al, J. Exp. Med., 160:1147 (1984); and B. Perussia et al, Natural Immunity and Cell Growth Regulation, 6:171–188 (1987).

c. ADCC Assay

In a standard antibody dependent cell mediated cytotoxity assay, preliminary results show that partially purified NKSF of the present invention enhanced NK cell killing of antibody coated tumor target cells in a dose dependent manner. For antibodies capable of binding to the Fc receptor of the NK cell, the ADCC response of NK cells was enhanced by the addition of NKSF.

d. Co-mitogenic effect of NKSF

PBLs ($0.5 \times 10^6$/ml) are cultured in 200 µl of RPMI 1640 medium supplemented with 10% heat inactivated human AB serum. After 3 and 6 days the PBLs are pulsed for 6 hours with $^3$H-thymidine and DNA synthesis (proliferation) is evaluated by the $^3$H-thymidine uptake in the cells by collecting the cells on glass filters using a Skatron cell harvester and counting the cell-associated $^3$H-Thymidine by liquid scintillation using a Packard Tricarb beta-counter. NKSF has minimal effect on PBL proliferation by itself, but is strongly co-mitogenic with phytohemagglutinin (PHA-M Welcome, 1:100) at day 6 of culture and with phorbol diesters (TPA or PDBu, $10^{-8}$ or $10^{-7}$M, respectively) at both day 3 and day 6. Cell cycle analysis is performed by flow cytofluorometry (Cytofluorograf 50H, Ortho Diagnostics) using a technique combining DNA staining with immunofluorescence staining according to London et al, *J. Immunol.*, 137:3845 (1986). This analysis has shown that the PBLs affected by the co-mitogenic effect of NKSF are T cells either CD4 or CD8 positive.

e. GM-CSF Induction Assay

Induction of GM-CSF expression in cultures of human PBLs was measured. In the assay, 100 µl of human PBLs suspended ($10^7$ cells/ml) in RPMI 1640 culture medium supplemented with 10% heat-inactivated FCS was added to 100 µl of sample to be tested in a microtiter plate [U-bottom, 96-well, Costar, Cambridge, Mass.] and incubated for 18 hours at 37° C., 5% $CO_2$. After incubation, 100 µl of cell-free supernatant was withdrawn from each well and the level of GM-CSF produced measured by enzyme-linked immunosorbent assay (ELISA) using two murine monoclonal antibodies against human GM-CSF (3/8.20.5 and 2/3.1, supplied by Genetics Institute, Inc.) recognizing different epitopes. Using recombinant human GM-CSF (Genetics Institute, Inc.) as a standard, the detection limit of this assay was 50 pg/ml.

Numerous modifications and variations in practice of this invention are expected to occur to those skilled in the art.

What is claimed is:

1. A monoclonal antibody which specifically reacts with natural killer cell stimulatory factor (NKSF) protein, wherein said protein has (a) a first subunit comprising the amino acid sequence of FIG. 1 from amino acids 23 to 328, and (b) a second subunit comprising the amino acid sequence of FIG. 2 from amino acid 57 to 253.

2. The antibody of claim 1, wherein said antibody reacts with said first subunit.

3. The antibody of claim 1, wherein said antibody reacts with said second subunit.

4. The antibody of claim 1, wherein said antibody is a murine antibody.

* * * * *